(12) United States Patent
Dattwyler et al.

(10) Patent No.: US 8,821,893 B2
(45) Date of Patent: Sep. 2, 2014

(54) **ORAL VACCINE FOR *BORRELIA***

(75) Inventors: Raymond J. Dattwyler, East Setauket, NY (US); Maria Gomes-Solecki, New York, NY (US)

(73) Assignee: Bio Peptides, Corp., East Setauket, NY (US)

( * ) Notice: Subject to any disclaimer, the term of this patent is extended or adjusted under 35 U.S.C. 154(b) by 805 days.

(21) Appl. No.: 11/631,090

(22) PCT Filed: Jun. 30, 2005

(86) PCT No.: PCT/US2005/023106
§ 371 (c)(1),
(2), (4) Date: Aug. 3, 2009

(87) PCT Pub. No.: WO2006/014292
PCT Pub. Date: Feb. 9, 2006

(65) Prior Publication Data
US 2009/0297560 A1    Dec. 3, 2009

Related U.S. Application Data

(60) Provisional application No. 60/585,057, filed on Jul. 2, 2004.

(51) Int. Cl.
*A61K 39/02* (2006.01)
*C12N 1/21* (2006.01)

(52) U.S. Cl.
USPC .................................. 424/235.1; 435/252.33

(58) Field of Classification Search
None
See application file for complete search history.

(56) References Cited

U.S. PATENT DOCUMENTS

| | | | | |
|---|---|---|---|---|
| 4,214,008 A * | 7/1980 | Groben et al. | ................... | 426/53 |
| 4,683,195 A | 7/1987 | Mullis et al. | ................. | 435/6.11 |
| 4,683,202 A | 7/1987 | Mullis | ........................... | 435/91.2 |
| 4,965,188 A | 10/1990 | Mullis et al. | ................. | 435/6.12 |
| 6,344,552 B1 * | 2/2002 | Flavell et al. | ................. | 536/23.7 |
| 6,676,942 B1 | 1/2004 | Lobet et al. | ................ | 424/190.1 |

FOREIGN PATENT DOCUMENTS

| | | | |
|---|---|---|---|
| EP | 1084709 | * | 3/2001 |
| WO | WO/01/21200 | | 2/2001 |
| WO | WO/02/16422 | | 2/2002 |
| WO | WO 02/16422 | * | 2/2002 |

OTHER PUBLICATIONS

Greenspan et al. (Nature Biotechnology 7: 936-937, 1999).*
Bowie et al (Science, 1990, 257:1306-1310).*
Fikrig et al (The Journal of Infectious Diseases, 1991:164:1224-1227).*
Hanson et al (Expert Rev. Vaccine, 2(5), 683-703, 1993).*
Willett et al (PNAS, Feb. 3, 2004, vol. 101, No. 5, p. 1303-1308).*
Abe, P. M. et al. (1978) Immunization of Mice Against *Fusobacterium necrophorum* Infection by Parenteral or Oral Administration of Vaccine, *Am. J. Vet. Res.* 39(1), 115-118.
Anderson, J. F. (1988) Mammalian and Avian Reservoirs for *Borrelia burgdorferi*, *Annals of the New York Academy of Sciences* 539(1), 180-191.
Anguita, J. et al. (2003) Adaptation of *Borrelia burgdorferi* in the tick and the mammalian host, *FEMS Microbiol. Rev.* 27(4), 493-504.
Balansky, R. et al. (1999) Inhibitory effects of freeze-dried milk fermented by selected *Lactobacillus bulgaricus* strains on carcinogenesis induced by 1,2-dimethylhydrazine in rats and by diethylnitrosamine in hamsters, *Cancer Letters* 147(1-2), 125-137.
Barbour, A. G. et al. (1993) The biological and social phenomenon of Lyme disease, *Science* 260(5114), 1610-1616.
Barthold, S. W. (1999) Specificity of Infection-Induced Immunity among *Borrelia burgdorferi* Sensu Lato Species, *Infection and Immunity* 67(1), 36-42.
Creekmore, T. et al. (2002) A baiting system for delivery of an oral plague vaccine to black-tailed prairie dogs, *J. Wildl. Dis.* 38(1), 32-39.
de Silva, A. M. et al. (1996) *Borrelia burgdorferi* OspA is an arthropod-specific transmission-blocking Lyme disease vaccine, *The Journal of Experimental Medicine* 183(1), 271-275.

(56) References Cited

OTHER PUBLICATIONS

Gerritse, K. et al. (1990) Oral administration of TNP-*Lactobacillus* conjugates in mice: A model for evaluation of mucosal and systemic immune responses and memory formation elicited by transformed lactobacilli, *Res. Microbiol.* 141(7-8), 955-962.

Gilmore, R. D. et al. (1996) Outer surface protein C (OspC), but not P39, is a protective immunogen against a tick-transmitted *Borrelia burgdorferi* challenge: evidence for a conformational protective epitope in OspC, *Infection and Immunity* 64(6), 2234-2239.

Gilmore, R. D. et al. (2000) Inhibition of *Borrelia burgdorferi* Migration from the Midgut to the Salivary Glands following Feeding by Ticks on OspC-Immunized Mice, *Infection and Immunity* 68(1), 411-414.

Grangette, C. et al. (2002) Protection against tetanus toxin after intragastric administration of two recombinant lactic acid bacteria: impact of strain viability and in vivo persistence, *Vaccine* 20(27-28), 3304-3309.

Gross, D. M. et al. (1998) Identification of LFA-1 as a candidate autoantigen in treatment-resistant Lyme arthritis, *Science* 281(5377), 703-706.

Gu, M. B. et al. (2001) Some observations in freeze-drying of recombinant bioluminescent *Escherichia coli* for toxicity monitoring, *J. Biotechnol.* 88(2), 95-105.

Guttman, D. S. et al. (1996) Multiple infections of *Ixodes scapularis* ticks by *Borrelia burgdorferi* as revealed by single-strand conformation polymorphism analysis, *Journal of Clinical Microbiology* 34(3), 652-656.

Hajishengallis, G. et al. (1995) Mucosal immunization with a bacterial protein antigen genetically coupled to cholera toxin A2/B subunits, *The Journal of Immunology* 154(9), 4322-4332.

Isolauri, E. et al. (1995) Improved immunogenicity of oral D x RRV reassortant rotavirus vaccine by *Lactobacillus casei* GG, *Vaccine* 13(3), 310-312.

Jauris-Heipke, S. et al. (1993) Genetic heterogenity of the genes coding for the outer surface protein C (OspC) and the flagellin of *Borrelia burgdorferi, Med. Microbiol. Immunol.* 182(1), 37-50.

Johnson, B. J. et al. (1995) Incomplete protection of hamsters vaccinated with unlipidated OspA from *Borrelia burgdorferi* infection is associated with low levels of antibody to an epitope defined by mAb LA-2, *Vaccine* 13(12), 1086-1094.

King, V. A. et al. (1998) Accelerated storage testing of freeze-dried and controlled low-temperature vacuum dehydrated *Lactobacillus acidophilus, J. Gen. Appl. Microbiol.* 44(2), 160-165.

Knobel, D. et al. (2002) Development of a bait and baiting system for delivery of oral rabies vaccine to free-ranging African wild dogs (*Lycaon pictus*), *J. Wildl. Dis.* 38(2), 352-362.

Lane, R. S. et al. (1991) Lyme Borreliosis: Relation of Its Causative Agent to Its Vectors and Hosts in North America and Europe, *Annu. Rev. Entomol.* 36(1), 587-609.

Lin, T. et al. (2002) Genetic Diversity of the Outer Surface Protein C Gene of Southern *Borrelia* Isolates and Its Possible Epidemiological, Clinical, and Pathogenetic Implications, *Journal of Clinical Microbiology* 40(7), 2572-2583.

Link-Amster, H. et al. (1994) Modulation of a specific humoral immune response and changes in intestinal flora mediated through fermented milk intake, *FEMS Immunol. Med. Microbiol.* 10(1), 55-63.

LoGiudice, K. et al. (2003) The ecology of infectious disease: Effects of host diversity and community composition on Lyme disease risk, *Proceedings of the National Academy of Sciences* 100(2), 567-571.

Luke, C. J. et al. (1997) Oral delivery of purified lipoprotein OspA protects mice from systemic infection with *Borrelia burgdorferi, Vaccine* 15(6-7), 739-746.

Maassen, C. B. M. et al. (1999) Instruments for oral disease-intervention strategies: recombinant *Lactobacillus casei* expressing tetanus toxin fragment C for vaccination or myelin proteins for oral tolerance induction in multiple sclerosis, *Vaccine* 17(17), 2117-2128.

Mather, T. N. et al. (1991) Absence of Transplacental Transmission of Lyme Disease Spirochetes from Reservoir Mice (*Peromyscus leucopus*) to their Offspring, *Journal of Infectious Diseases* 164(3), 564-567.

McGrath, B. C. et al. (1995) Identification of an immunologically important hypervariable domain of major outer surface protein A of *Borrelia burgdorferi, Infection and Immunity* 63(4), 1356-1361.

McIntosh, G. H. et al. (1999) A Probiotic Strain of *L. acidophilus* Reduces DMH-Induced Large Intestinal Tumors in Male Sprague-Dawley Rats, *Nutrition and Cancer* 35(2), 153-159.

Mowat, A. M. (1985) The role of antigen recognition and suppressor cells in mice with oral tolerance to ovalbumin, *Immunology* 56(2), 253-260.

Needleman, S. B. et al. (1970) A general method applicable to the search for similarities in the amino acid sequence of two proteins, *J. Mol. Biol.* 48(3), 443-453.

Ohnishi, J. et al. (2001) Antigenic and genetic heterogeneity of *Borrelia burgdorferi* populations transmitted by ticks, *Proceedings of the National Academy of Sciences* 98(2), 670-675.

Ostfeld, R. S. et al. (1996) Temporal and spatial dynamics of *Ixodes scapularis* (Acari: Ixodidae) in a rural landscape, *J. Med. Entomol.* 33(1), 90-95.

Ostfeld, R. S. et al. (2000) Pulsed resources and community dynamics of consumers in terrestrial ecosystems, *Trends in ecology & evolution (Personal edition)* 15(6), 232-237.

Ostfeld, R. S. et al. (2001) Effects of acorn production and mouse abundance on abundance and *Borrelia burgdorferi* infection prevalence of nymphal *Ixodes scapularis* ticks, *Vector Borne Zoonot. Dis.* 1(1), 55-63.

Pal, U. et al. (2000) Attachment of *Borrelia burgdorferi* within *Ixodes scapularis* mediated by outer surface protein A, *The Journal of Clinical Investigation* 106(4), 561-569.

Pal, U. et al. (2001) Inhibition of *Borrelia burgdorferi*-Tick Interactions In Vivo by Outer Surface Protein A Antibody, *The Journal of Immunology* 166(12), 7398-7403.

Pavlova, S. I. et al. (2002) Characterization of a cryptic plasmid from *Lactobacillus fermentum* KC5b and its use for constructing a stable *Lactobacillus* cloning vector, *Plasmid* 47(3), 182-192.

Pearson, W. R. et al. (1988) Improved tools for biological sequence comparison, *Proceedings of the National Academy of Sciences* 85(8), 2444-2448.

Piesman, J. (1993) Dynamics of *Borrelia burgdorferi* Transmission by Nymphal *Ixodes dammini* Ticks, *Journal of Infectious Diseases* 167(5), 1082-1085.

Pospisilik, J. A. et al. (2003) Dipeptidyl Peptidase IV Inhibitor Treatment Stimulates β-Cell Survival and Islet Neogenesis in Streptozotocin-Induced Diabetic Rats, *Diabetes* 52(3), 741-750.

Pouwels, P. H. et al. (1996) The potential of *Lactobacillus* as a carrier for oral immunization: Development and preliminary characterization of vector systems for targeted delivery of antigens, *J. Biotechnol.* 44(1-3), 183-192.

Prasad, J. et al. (2003) Heat and Osmotic Stress Responses of Probiotic *Lactobacillus rhamnosus* HN001 (DR20) in Relation to Viability after Drying, *Appl. Environ. Microbiol.* 69(2), 917-925.

Qiu, W.-G. et al. (2002) Geographic Uniformity of the Lyme Disease Spirochete (*Borrelia burgdorferi*) and Its Shared History With Tick Vector (*Ixodes scapularis*) in the Northeastern United States, *Genetics* 160(3), 833-849.

Rangavajhyalaa, N. et al. (1997) Nonlipopolysaccharide components) of *Lactobacillus addophilus* stimulate(s) the production of interleukin-1α and tumor necrosis factor-α by murine macrophages, *Nutrition and Cancer* 28(2), 130-134.

Reveneau, N. et al. (2002) Comparison of the immune responses induced by local immunizations with recombinant *Lactobacillus plantarum* producing tetanus toxin fragment C in different cellular locations, *Vaccine* 20(13-14), 1769-1777.

Šadžiene, A. et al. (1993) In Vitro Inhibition of *Borrelia burgdorferi* Growth by Antibodies, *Journal of Infectious Diseases* 167(1), 165-172.

Sambrook, J. et al. (1989) in *Molecular Cloning: A Laboratory Manual* (Sambrook, J., et al., Eds.) 2nd ed., pp. 9.31-9.58, Cold Spring Harbor Laboratory Press, New York.

(56) References Cited

OTHER PUBLICATIONS

Sambrook, J. et al. (1989) in *Molecular Cloning: A Laboratory Manual* (Sambrook, J., et al., Eds.) 2nd ed., pp. 7.39-37.52, Cold Spring Harbor Laboratory Press, New York.

Schaible, U. E. et al. (1990) Monoclonal antibodies specific for the outer surface protein A (OspA) of *Borrelia burgdorferi* prevent Lyme borreliosis in severe combined immunodeficiency (scid) mice, *Proceedings of the National Academy of Sciences* 87(10), 3768-3772.

Scheppler, L. et al. (2002) Recombinant *Lactobacillus johnsonii* as a mucosal vaccine delivery vehicle, *Vaccine* 20(23-24), 2913-2920.

Schubach, W. H. et al. (1991) Mapping antibody-binding domains of the major outer surface membrane protein (OspA) of *Borrelia burgdorferi*, *Infection and Immunity* 59(6), 1911-1915.

Schwan, T. G. et al. (1995) Induction of an outer surface protein on *Borrelia burgdorferi* during tick feeding, *Proceedings of the National Academy of Sciences* 92(7), 2909-2913.

Seinost, G. et al. (1999) Four Clones of *Borrelia burgdorferi* Sensu Stricto Cause Invasive Infection in Humans, *Infection and Immunity* 67(7), 3518-3524.

Shaw, D. M. et al. (2000) Engineering the microflora to vaccinate the mucosa: serum immunoglobulin G responses and activated draining cervical lymph nodes following mucosal application of tetanus toxin fragment C-expressing lactobacilli, *Immunology* 100(4), 510-518.

Sigal, L. H. et al. (1998) A Vaccine Consisting of Recombinant *Borrelia burgdorferi* Outer-Surface Protein A to Prevent Lyme Disease, *New England Journal of Medicine* 339(4), 216-222.

Simon, M. M. et al. (1991) Recombinant Outer Surface Protein A from *Borrelia burgdorferi* Induces Antibodies Protective against Spirochetal Infection in Mice, *Journal of Infectious Diseases* 164(1), 123-132.

Smith, T. F. et al. (1981) Comparison of biosequences, *Advances in Applied Mathematics* 2(4), 482-489.

Southey, A. et al. (2002) Sulfadimethoxine and rhodamine B as oral biomarkers for European badgers (*Meles meles*), *J. Wildl. Dis.* 38(2), 378-384.

Steere, A. C. et al. (1998) Vaccination against Lyme Disease with Recombinant *Borrelia burgdorferi* Outer-Surface Lipoprotein A with Adjuvant, *New England Journal of Medicine* 339(4), 209-215.

Stevenson, B. et al. (1994) Expression and sequence of outer surface protein C among North American isolates of *Borrelia burgdorferi*, *FEMS Microbiol. Lett.* 124(3), 367-372.

Stevenson, B. et al. (1995) Temperature-related differential expression of antigens in the Lyme disease spirochete, *Borrelia burgdorferi*, *Infection and Immunity* 63(11), 4535-4539.

Strobel, S. et al. (1983) Immunological responses to fed protein antigens in mice. II. Oral tolerance for CMI is due to activation of cyclophosphamide-sensitive cells by gut-processed antigen, *Immunology* 49(3), 451-456.

Suda, Y. et al. (1995) Cytokine-inducing glycolipids in the lipoteichoic acid fraction from *Enterococcus hirae* ATCC 9790, *FEMS Immunol. Med. Microbiol.* 12(2), 97-112.

Wang, G. et al. (2002) Disease Severity in a Murine Model of Lyme Borreliosis Is Associated with the Genotype of the Infecting *Borrelia burgdorferi* Sensu Stricto Strain, *Journal of Infectious Diseases* 186(6), 782-791.

Wang, I.-N. et al. (1999) Genetic Diversity of ospC in a Local Population of *Borrelia burgdorferi* sensu stricto, *Genetics* 151(1), 15-30.

Wilske, B. et al. (1992) Molecular analysis of the outer surface protein A (OspA) of *Borrelia burgdorferi* for conserved and variable antibody binding domains, *Med. Microbiol. Immunol.* 181(4), 191-207.

Wilske, B. et al. (1993) Immunological and molecular polymorphisms of OspC, an immunodominant major outer surface protein of *Borrelia burgdorferi*, *Infection and Immunity* 61(5), 2182-2191.

PCT International Search Report of International Application No. PCT/US2005/023106 dated Jun. 1, 2006.

Tsao, J. et al. (2001) "OspA immunization decreases transmission of *Borrelia burgdorferi* spirochetes from infected *Peromyscus leucopus* mice to larval *Ixodes scapularis* ticks," *Vector Borne and Zoonotic Diseases* 1(1), 65-74.

\* cited by examiner

A

ATGAAAAAATATTTATTGGGAATAGGTCTAATATTAGCCTTAATAGCATGTAAGCAAAATGTTAGCAGCC
TTGACGAGAAAAACAGCGTTTCAGTAGATTTGCCTGGTGAAATGAAAGTTCTTGTAAGCAAAGAAAAAAA
CAAAGACGGCAAGTACGATCTAATTGCAACAGTAGACAAGCTTGAGCTTAAAGGAACTTCTGATAAAAAC
AATGGATCTGGAGTACTTGAAGGCGTAAAAGCTGACAAAAGTAAAGTAAAATTAACAATTTCTGACGATC
TAGGTCAAACCACACTTGAAGTTTTCAAAGAAGATGGCAAAACACTAGTATCAAAAAAAGTAACTTCCAA
AGACAAGTCATCAACAGAAGAAAAATTCAATGAAAAAGGTGAAGTATCTGAAAAAATAATAACAAGAGCA
GACGGAACCAGACTTGAATACACAGGAATTAAAAGCGATGGATCTGGAAAAGCTAAAGAGGTTTTAAAAG
GCTATGTTCTTGAAGGAACTCTAACTGCTGAAAAAACAACATTGGTGGTTAAAGAAGGAACTGTTACTTT
AAGCAAAAATATTTCAAATCTGGGGAAGTTTCAGTTGAACTTAATGACACTGACAGTAGTGCTGCTACT
AAAAAAACTGCAGCTTGGAATTCAGGCACTTCAACTTTAACAATTACTGTAAACAGTAAAAAAACTAAAG
ACCTTGTGTTTACAAAAGAAAACACAATTACAGTACAACAATACGACTCAAATGGCACCAAATTAGAGGG
GTCAGCAGTTGAAATTACAAAACTTGATGAAATTAAAAACGCTTTAAAATAA

B

MKKYLLGIGL ILALIACKQN VSSLDEKNSV SVDLPGEMKV LVSKEKNKDG KYDLIATVDK
LELKGTSDKN NGSGVLEGVK ADKSKVKLTI SDDLGQTTLE VFKEDGKTLV SKKVTSKDKS
STEEKFNEKG EVSEKIITRA DGTRLEYTGI KSDGSGKAKE VLKGYVLEGT LTAEKTTLVV
KEGTVTLSKN ISKSGEVSVE LNDTDSSAAT KKTAAWNSGT STLTITVNSK KTKDLVFTKE
NTITVQQYDS NGTKLEGSAV EITKLDEIKN ALK

C

ATGAAAAAGAATACATTAAGTGCGATATTAATGACTTTATTTTTATTTATATCTTGTAATAATTCAGGGA
AAGATGGGAATACATCTGCAAATTCTGCTGATGAGTCTGTTAAAGGGCCTAATCTTACAGAAATAAATAA
AAAAATTACGGATTCTAATGCGGTTTTACTTGCTGTGAAAGAGGTTGAAGCGTTGCTGTCATCTATAGAT
GAAATTGCTGCTAAAGCTATTGGTAAAAAAATACACCAAAATAATGGTTTGGATACCGAAAATAATCACA
ATGGATCATTGTTAGCGGGAGCTTATGCAATATCAACCCTAATAAAACAAAAATTAGATGGATTGAAAAA
TGAAGGATTAAAGGAAAAAATTGATGCGGCTAAGAAATGTTCTGAAACATTTACTAATAAATTAAAAGAA
AAACACACAGATCTTGGTAAAGAAGGTGTTACTGATGCTGATGCAAAAGAAGCCATTTTAAAAGCAAATG
GTACTAAAACTAAAGGTGCTGAAGAACTTGGAAAATTATTTGAATCAGTAGAGGTCTTGTCAAAAGCAGC
TAAAGAGATGCTTGCTAATTCAGTTAAAGAGCTTACAAGCCCTGTTGTGGCAGAAAGTCCAAAAAAACCT
TAA

D

MKKNTLSAIL MTLFLFISCN NSGKDGNTSA NSADESVKGP NLTEINKKIT DSNAVLLAVK
EVEALLSSID EIAAKAIGKK IHQNNGLDTE NNHNGSLLAG AYAISTLIKQ KLDGLKNEGL
KEKIDAAKKC SETFTNKLKE KHTDLGKEGV TDADAKEAIL KANGTKTKGA EELGKLFESV
EVLSKAAKEM LANSVKELTS PVVAESPKKP

FIG. 6

ORAL VACCINE FOR *BORRELIA*

This invention was made with government support under grant number 1R44AI58364 awarded by the National Institutes of Health (NIH). The government has certain rights in the invention.

FIELD OF THE INVENTION

The present invention relates to vaccines for control of *Borrelia* infections in animal and human populations. In particular, the present invention provides compositions and methods comprising recombinant bacteria engineered to express one or more *Borrelia burgdorferi* antigens for use as Lyme disease vaccines. In some embodiments, the recombinant bacteria are freeze-dried.

BACKGROUND OF THE INVENTION

Lyme disease is caused by the spirochete *Borrelia burgdorferi*, a gram-negative bacterium transmitted to animals and humans by infected ticks of the *Ixodes* genus. Lyme disease is characterized by the presence of the classic bull's-eye rash surrounding the tick bite, erythema migrans, accompanied by nonspecific symptoms such as fever, malaise, fatigue, headache, and myalgia. *B. burgdorferi* infection in the untreated or inadequately treated patient may progress to disseminated disease. Manifestations of disseminated disease occur in two phases. The first phase occurring days to weeks after infection includes neurological symptoms and/or cardiac dysfunction, while the second phase occurring weeks to months after infection includes arthralgias and arthritis.

Lyme disease has rapidly emerged as the most prevalent zoonotic vector-borne infectious disease in the United States, and its geographical range is expanding. In 2002, nearly 24,000 cases of Lyme disease were reported to the Centers for Disease Control and Prevention (MMWR, 52:741-750, 2003), and more than 150,000 cases have been reported to U.S. health authorities since 1982, when a systematic national surveillance was initiated. The regrowth of natural forests from farmland in the Northeastern United States in the twentieth century has created conditions conducive to the spread of human Lyme disease. Suburban communities are now often adjacent to forested areas where *Ixodes scapularis* populations thrive along with deer (*Odocoileus virginianus*) and white-footed mice (*Peromyscus leucopus*), known to be the major natural reservoir for *B. burgdorferi*. Methods to control *B. burgdorferi* through acaricide or antimicrobial agents are limited and many, such as organochlorine pesticides, have had negative environmental and human health effects sufficient to outlaw their use.

The development of a highly specific, easily distributable, economically viable wildlife vaccine to be used to reduce the prevalence of *B. burgdorferi* in ticks and in animal reservoirs surrounding human communities could quickly and significantly reduce the incidence of Lyme disease cases. Such a vaccine would also be desirable for use in domesticated animals including species of agricultural importance, as well as species kept as pets.

Additionally, an oral Lyme disease vaccine for human consumption would be a pleasing alternative to traditional intramuscular or intradermal vaccines, for preventing human morbidity associated with bites from *B. burgdorferi*-infected ticks.

SUMMARY OF THE INVENTION

The present invention relates to vaccines for control of *Borrelia* infections in animal and human populations. In particular, the present invention provides compositions and methods comprising recombinant bacteria engineered to express one or more *Borrelia burgdorferi* antigens for use as Lyme disease vaccines. In some embodiments, the recombinant bacteria are freeze-dried.

The present invention provides compositions comprising a bacterium engineered to express at least one outer surface protein of *Borrelia burgdorferi*. In some embodiments, the bacterium comprises lyophilized *E. coli*, while in other embodiments, the bacterium comprises a *lactobacillus* selected from the group consisting of *L. acidophilus, L. brevis, L. casei, L. crispatus, L. fermentum, L. gasseri, L. plantarum, L. reuteri, L. rhamnzosus,* and *L. salivarius*. In some particularly preferred embodiments, the *lactobacillus* comprises *L. plantarum*. In some embodiments, the at least one outer surface protein comprises an OspA fragment of at least 100 amino acids that is at least 90% identical to the amino acid sequence set forth as SEQ ID NO:2, or an OspA fragment of at least 200 amino acids that is at least 80% identical to the amino acid sequence set forth as SEQ U) NO:2. In some preferred embodiments, the at least one outer surface protein comprises an OspA fragment with a mutated hLFA1 epitope. In other embodiments, the at least one outer surface protein comprises an OspC fragment of at least 100 amino acids that is at least 80% identical to the amino acid sequence set forth as SEQ ID NO:4 or an OspC fragment of at least 150 amino acids that is at least 85% identical to the amino acid sequence set forth as SEQ ID NO:4. In some preferred embodiments, the at least one outer surface protein comprises one or both of an OspC1 type fragment and OspC12 type fragment. In other preferred embodiments, the at least one outer surface protein comprises a chimeric protein comprising two or more of an OspA fragment, an OspC1 type fragment, and an OspC12 type fragment. Also provided are embodiments in which the outer surface protein comprises one or more of an OspC4 type fragment, an OspC6 type fragment, and an OspC8 type fragment.

In addition, the present invention provides oral vaccine compositions comprising at least one bacterium engineered to express at least one *Borrelia burgdorferi* outer surface protein, and a food carrier or an excipient. In some embodiments, the bacterium is selected from the group consisting of *Escherichia coli*, and *Lactobacillus plantarum*. In a subset of the embodiments, the bacterium is lyophilized. In preferred embodiments, the food carrier comprises a dairy product selected from the group consisting of milk, yoghurt, and cheese, or a grain product selected from the group consisting of grain, seed, bread, and cereal. In other preferred embodiments, the excipient is selected from the group consisting of a sugar, a starch, a gum, and a protein. In some embodiments, the food carrier comprises animal chow. Also provided are devices for administering an oral vaccine to a rodent, comprising an oral vaccine composition comprising at least one bacterium engineered to express at least one *Borrelia burgdorferi* outer surface protein, and a food carrier or an excipient, contained within a small sealed container having an opening suitable for access by small rodents. Moreover, the present invention provides kits comprising an oral vaccine composition comprising at least one bacterium engineered to express at least one *Borrelia burgdorferi* outer surface protein, and a food carrier or an excipient, and instructions for orally administering the oral vaccine composition.

The present invention also provides methods of immunizing a subject comprising: providing an oral vaccine composition comprising a bacterium engineered to express at least one *Borrelia burgdorferi* outer surface protein; and feeding the oral vaccine composition to a subject under conditions suitable for eliciting an antibody response in the subject against the at least one *Borrelia burgdorferi* outer surface protein. In some embodiments, the bacterium is selected from the group consisting of *Escherichia coli*, and *Lactobacillus plantarum*. In a subset of the embodiments the bacterium is lyophilized. In some preferred embodiments, the oral vaccine composition further comprises a food carrier or an excipient. In particularly preferred embodiments, the subject is a mammal. However, the invention is not limited to mammals. In fact, embodiments of the invention are contemplated to be suitable for delivery to an avian subject. The invention provides embodiments in which the mammal is a feral animal comprising one or more of a mouse, a chipmunk, a squirrel, a shrew, a vole, a rat, a raccoon, an opossum, a skunk, a rabbit, and a deer. Alternatively, the invention provides embodiments in which the mammal is a domesticated animal comprising one or more of a dog, a cat, a cow, and a horse. In some particularly preferred embodiments, the mammal is a human. Other preferred embodiments comprise methods in which the antibody response comprises an outer surface protein-reactive serum IgG titer of at least 1:100, and/or an outer surface protein-reactive mucosal IgA titer of at least 1:10. In some preferred embodiments, the feeding comprises more than one meal. In a subset of the embodiments, the feeding is done by oral gavage.

Furthermore, the present invention provides compositions comprising a nonpathogenic vector bacterium engineered to express at least one antigen of a pathogenic bacterium. In some embodiments, the nonpathogenic vector bacterium is selected from the group consisting of *Escherichia coli*, and *Lactobacillus plantarum*. In a subset of the embodiments, the vector bacterium is lyophilized. In some preferred embodiments, the pathogenic bacterium is selected from the group consisting of *Yersinia pestis*, and *Rickettsia rickettsii*. In some embodiments in which the pathogenic bacterium is *Yersinia pestis*, the at least one antigen is selected from the group consisting of Caf1 and LcrV. Likewise, in some embodiments in which the pathogenic bacterium is *Rickettsia rickettsi*, the at least one antigen is selected from the group consisting of OmpA and OmpB. In other preferred embodiments, the pathogenic bacterium is selected from but not limited to *Bacillus anthracis, Escherichia coli* O157:H7, *Helicobacter pylori, Neisseria gonorrhoeae, Pseudomonas aeruginosa, Streptococcus pneumoniae, Haemophilus influenzae* type b, *Moraxella catarrhalis, Salmonella enterica, Salmonella enteritides*, and *Vibrio cholera*. In some embodiments, fragments of the antigen(s) of interest retain their own leader sequence or lack a leader sequence entirely.

Additionally, the present invention provides methods for producing an oral vaccine comprising: providing at least one bacterium engineered to express at least one *Borrelia burgdorferi* outer surface protein; and lyophilizing the bacterium to produce at least one lyophilized bacterium. Some embodiments further comprise contacting the at least one bacterium with IPTG under conditions suitable for inducing heightened expression of the at least one *Borrelia burgdorferi* outer surface protein prior to lyophilization. Preferred embodiments further comprise admixing the lyophilized bacterium with a food carrier or an excipient. A subset of the embodiments, further comprise paraffinizing the lyophilized bacterium.

BRIEF DESCRIPTION OF THE FIGURES

FIG. 6 provides the sequences of OspA and OspC of *B. burgdorferi* strain B31. The nucleic acid sequence of OspA (SEQ ID NO:1) is provided in panel A, while the amino acid sequence of OspA (SEQ ID NO:2) is provided in panel B. The nucleic-acid sequence of OspC1 (SEQ ID NO:3) is provided in panel C, while the amino acid sequence of OspC1 (SEQ ID NO:4) is provided in panel D.

DEFINITIONS

Figure 1:
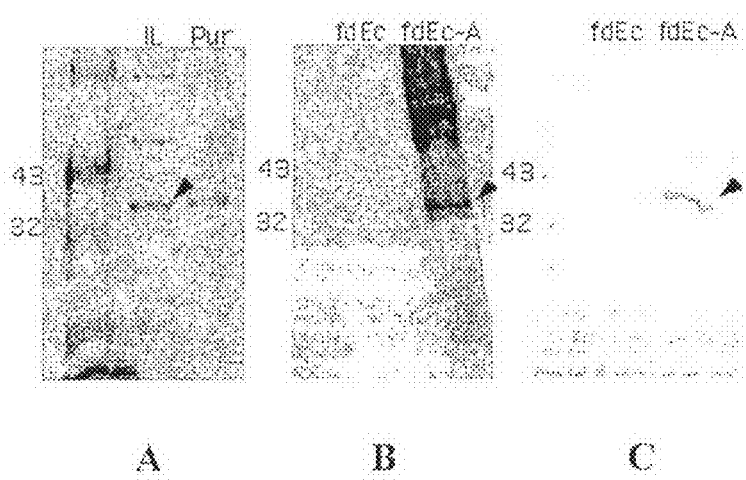
FIG. 1 depicts the expression of *B. burgdorferi* OspA by transformed *E. coli*. Panel A shows a Coomassie stained SDS-PAGE gel of a freshly induced culture, panel B shows a Coomassie stained SDS-PAGE gel of a freeze dried culture, and panel C shows a western blot of the freeze dried culture probed with the anti-OspA mAb, LA2.2. Abbreviations are as follows: IL, induced lysate; Pur, purified; fd, freeze dried; Ec, *E. coli*; and Ec-A, *E. coli*-expressing OspA.

The term "gene" refers to a nucleic acid (e.g., DNA) sequence that comprises coding sequences necessary for the production of a polypeptide or precursor or RNA (e.g., tRNA, siRNA, rRNA, etc.). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the sequences located adjacent to the coding region on both the 5' and 3' ends, such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region, which may be interrupted with non-coding sequences termed "introns" or "intervening regions" or "intervening sequences." Introns are removed or "spliced out" from the nuclear or primary transcript, and are therefore absent in the messenger RNA (mRNA) transcript. The mRNA functions during translation to specify the sequence or order of amino acids in a nascent polypeptide.

In particular, the term "OspA gene" refers to the full-length *B. burgdorferi* outer surface protein A nucleotide sequence. However, it is also intended that the term encompass fragments of the OspA-sequence, and/or other domains within the full-length OspA nucleotide sequence (e.g., coding region set forth in SEQ ID NO:1). Furthermore, the terms "OspA nucleotide sequence" or "OspA polynucleotide sequence" encompasses DNA, cDNA, and RNA (e.g., mRNA) sequences.

Similarly, the term "OspC gene" refers to the full-length *B. burgdorferi* outer surface protein C nucleotide sequence. However, it is also intended that the term encompass fragments of the OspC sequence, and/or other domains within the full-length OspC nucleotide sequence (e.g., coding region set forth in SEQ ID NO:3). Furthermore, the terms "OspC nucleotide sequence" or "OspC polynucleotide sequence" encompasses DNA, cDNA, and RNA (e.g., mRNA) sequences.

The term "plasmid" as used herein, refers to a small piece of extrachromosomal cytoplasmic DNA, capable of autonomous replication. Similarly, the term "naked plasmid" refers to plasmid DNA devoid of extraneous material typically used to affect transfection. As used herein, a "naked plasmid" refers to a plasmid substantially free of calcium-phosphate, DEAE-dextran, liposomes, and/or polyamines.

As used herein, the term "purified" refers to molecules (polynucleotides or polypeptides) that are removed from their natural environment, isolated or separated. "Purified" molecules are at least 50% free, preferably at least 75% free, and more preferably at least 90% free from other components with which they are naturally associated.

The term "recombinant DNA" refers to a DNA molecule that is comprised of segments of DNA joined together by means of molecular biology techniques. Similarly, the term "recombinant protein" refers to a protein molecule that is expressed from recombinant DNA.

The term "fusion protein" as used herein refers to a protein formed by expression of a hybrid gene made by combining two gene sequences. Typically this is accomplished by cloning a cDNA into an expression vector in frame with an existing gene. The fusion partner may act as a reporter (e.g., βgal) or may provide a tool for isolation purposes (e.g., GST).

Suitable systems for production of recombinant proteins include but are not limited to prokaryotic (e.g., *Escherichia coli*), yeast (e.g., *Saccaromyces cerevisiae*), insect (e.g., baculovirus), mammalian (e.g., Chinese hamster ovary), plant (e.g., safflower), and cell-free systems (e.g., rabbit reticulocyte lysate).

As used herein, the term "coding region" refers to the nucleotide sequences that encode the amino acid sequences found in the nascent polypeptide as a result of translation of an mRNA molecule. The coding region is bounded in eukaryotes, on the 5' side by the nucleotide triplet "ATG" that encodes the initiator methionine and on the 3' side by one of the three triplets which specify stop codons (i.e., TAA, TAG, and TGA).

Where "amino acid sequence" is recited herein to refer to an amino acid sequence of a protein molecule, "amino acid sequence" and like terms such as "polypeptide" or "protein" are not meant to limit the amino acid sequence to the complete, native amino acid sequence associated with the recited protein molecule. Rather the terms "amino acid sequence" and "protein" encompass partial sequences, and modified sequences.

The term "wild type" refers to a gene or gene product that has the characteristics of that gene or gene product when isolated from a naturally occurring source. A wild type gene is that which is most frequently observed in a population and is thus arbitrarily designated the "normal" or "wild-type" form of the gene.

In contrast, the terms "modified," "mutant," and "variant" refer to a gene or gene product that displays modifications in sequence and or functional properties (i.e., altered characteristics) when compared to the wild-type gene or gene product. In some embodiments, the modification comprises at least one insertion, deletion, or substitution. In preferred embodiments, the modification comprises removal of the hLFA epitope, YVLEGTLTA (SEQ ID NO:5), from OspA by deletion or substitution of one or more amino acid residues.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to reduction in binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe Will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

As used herein, the term "competes for binding" when used in reference to a first and a second polypeptide means that the first polypeptide with an activity binds to the same substrate as does the second polypeptide with an activity. In one embodiment, the second polypeptide is a variant of the first polypeptide (e.g., encoded by a different allele) or a related (e.g., encoded by a homolog) or dissimilar (e.g., encoded by a second gene having no apparent relationship to the first gene) polypeptide. The efficiency (e.g., kinetics or thermodynamics) of binding by the first polypeptide may be the same as or greater than or less than the efficiency of substrate binding by the second polypeptide. For example, the equilibrium binding constant ($K_D$) for binding to the substrate may be different for the two polypeptides. The term "$K_m$" as used herein refers to the Michaelis-Menten constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% \text{ G+C})$, when a nucleic acid is in aqueous solution at 1 M NaCl (See e.g., Anderson and Young, Quantitative Filter Hybridization, *in Nucleic Acid Hybridization*, 1985). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with 85-100% identity, preferably 70-100% identity). With medium stringency conditions, nucleic acid base pairing will occur between nucleic acids with an intermediate frequency of complementary base sequences (e.g., hybridization under "medium stringency" conditions may occur between homologs with 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution comprising 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 100 to about 1000 nucleotides in length is employed.

"Medium stringency conditions" when used in reference to nucleic acid hybridization comprise conditions equivalent to binding or hybridization at 42° C. in a solution comprising 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 1.0×SSPE, 1.0% SDS at 42° C. when a probe of about 100 to about 1000 nucleotides in length is employed.

"Low stringency conditions" comprise conditions equivalent to binding or hybridization at 42° C. in a solution comprising 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 μg/ml denatured salmon sperm DNA followed by washing in a solution comprising 5×SSPE, 0.1% SDS at 42° C. when a probe of about 100 to about 1000 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 85% to 95% homology to the first nucleic acid sequence, then another hybridization condition is said to be equivalent to the hybridization condition of interest if this other hybridization condition also results in hybridization of the first nucleic acid sequence with the other nucleic acid sequences that have from 85% to 95% homology to the first nucleic acid sequence.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv Appl Math, 2: 482, 1981), by the homology alignment algorithm of Needleman and Wunsch (Needleman and Wunsch, J Mol Biol, 48:443, 1970), by the search for similarity method of Pearson and Lipman (Pearson and Lipman, Proc Natl Acad Sci USA, 85:2444, 1988), by computerized implementations of these algorithms (GAP, BESTFIT, FASTA, and TFASTA in the Wisconsin Genetics Software Package Release 7.0, Genetics Computer Group, Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., OspA)

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having acidic side chains is glutamic acid and aspartic acid; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acids. Amplification techniques have been designed primarily for this sorting out.

Template specificity is achieved in most amplification techniques by the choice of enzyme. Amplification enzymes are enzymes that under the conditions they are used, will process only specific sequences of nucleic acid in a heterogeneous mixture of nucleic acid. In particular, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular OspA sequences. It is contemplated that any probe used in the present invention will be labelled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of Mullis (U.S. Pat. Nos. 4,683,195, 4,683,202, and 4,965,188, hereby incorporated by reference). The patents describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

As used herein, the terms "restriction endonucleases" and "restriction enzymes" refer to bacterial enzymes, each of which cut double-stranded DNA at or near a specific nucleotide sequence.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a gene includes, by way of example, such nucleic acid in cells ordinarily expressing the gene, but where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

The terms "fragment" and "portion" when used in reference to a nucleotide sequence (as in "a portion of a given nucleotide sequence") refer to partial segments of that sequence. The fragments may range in size from four nucleotides to the entire nucleotide sequence minus one nucleotide (10 nucleotides, 20, 30, 40, 50, 100, 200, etc.).

Similarly, the terms "fragment" and "portion" when used in reference to a polypeptide sequence refers to partial segments of that sequence. In some embodiments, the portion has an amino-terminal and/or carboxy-terminal deletion as compared to the native protein, but the remaining amino acid sequence is identical to the corresponding positions in the amino acid sequence deduced from a full-length cDNA sequence. Fragments are preferably at least 4 amino acids long, more preferably at least 50 amino acids long, and most preferably at least 50 amino acids long or longer (the entire amino acid sequence minus on amino acid). In particularly preferred embodiments, the portion comprises the amino acid residues required for intermolecular binding of the compositions of the present invention with its various ligands and/or substrates.

As used herein the term "coding region" when used in reference to a structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets, which specify stop codons (i.e., TAA, TAG, TGA).

As used herein, the term "purified" refers to molecules (polynucleotides or polypeptides) that are separated from other components with which they are naturally associated. "To purify" refers to a reduction (preferably by at, least 10%, more preferably by at least 50%, and most preferably by at least 90%) of one or more contaminants in a sample. For example, OspA antibodies are purified by removal of contaminating non-immunoglobulin proteins; they are also purified by the removal of immunoglobulin that does not bind OspA. The removal of non-immunoglobulin proteins and/or the removal of immunoglobulins that do not bind OspA will result in an increase in the percent of OspA-reactive immunoglobulins in the sample. In another example, recombinant OspA polypeptides are expressed in bacterial host cells and the polypeptides are purified by the removal of host cell proteins; the percent of recombinant OspA polypeptides is thereby increased in the sample.

The term "recombinant DNA molecule" as used herein refers to a DNA molecule that is comprised of segments of DNA joined together by means of molecular biological techniques. Similarly, the term "recombinant protein" or "recombinant polypeptide" as used herein refers to a protein molecule that is expressed from a recombinant DNA molecule.

The term "native protein" as used herein refers to a protein that does not contain amino acid residues encoded by vector sequences. That is the native protein contains only those amino acids found in the protein as it occurs in nature. A native protein may be produced by recombinant means or may be isolated from a naturally occurring source.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook et al., *Molecular Cloning: A Laboratory Manual*, Cold Spring Harbor Press, NY, pp 9.31-9.58, 1989).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al., supra, pp 7.39-7.52, 1989).

The term "Western blot" refers to the analysis of protein(s) (or polypeptides) immobilized onto a support such as nitrocellulose or a membrane. The proteins are electrophoresed through an acrylamide gel to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The terms "antigenic determinant" and "epitope" as used herein refer to that portion of an antigen that makes contact with a particular antibody and/or T cell receptor. When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign gene that is placed into an organism by introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same chromosomal location as does the naturally occurring gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome-binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The basic technique is modified to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding OspA or fragments thereof may be employed as hybridization probes. In this case, the OspA encoding polynucleotide sequences are typically employed in an aqueous solution containing salts (e.g., NaCl), detergents (e.g., SDS), and other components (e.g., Denhardt's solution, dry milk, salmon sperm DNA, etc.).

As used herein, the terms "*Borrelia burgdorferi*" and "*B. burgdorferi*" refer to a gram-negative helical bacterium (spirochete) that is the aetiologic agent of Lyme disease, and which is generally transmitted to its vertebrate hosts by several species of *Ixodid* ticks. As used herein, the term "*Borrelia burgdorferi*" encompasses the members of the *Borrelia burgdorferi* sensu lato group including the species: *B. burgdorferi* sensu stricto; *Borrelia garinii*; and *Borrelia afzelii*.

The terms "Lyme disease" and "Lyme borreliosis" refer to a bacterial disease caused by the microorganism (spirochete) *Borrelia burgdorferi*. Symptoms include a large circular red rash at the bite site (50-60% of cases), malaise, fever, headache, muscle aches and swollen lymph nodes. If untreated, these symptoms may progress to arthritis and compromise heart function.

The terms "OspA" and "outer surface protein A" as used herein refer to one of the major membrane lipoproteins of *Borrelia burgdorferi*, exemplified by the OspA amino acid sequence of SEQ ID NO:2 (the corresponding OspA coding region is exemplified by SEQ ID NO:1).

The terms "OspC" and "outer surface protein C" as used herein refer to one of the major membrane lipoproteins of *Borrelia burgdorferi*, exemplified by the OspC1 amino acid sequence of SEQ ID NO:4 (the corresponding OspC coding region is exemplified by SEQ ID NO:3).

The term "chimera" as used in reference to a *Borrelia burgdorferi* outer surface protein, refers to a recombinant fusion protein of two or more *Borrelia burgdorferi* outer surface proteins (e.g., OspA/C1, OspA/C12, OspC1/C12, etc.).

The term "pathogenic bacteria" refers to bacteria that cause disease in a subject of interest. In contrast, the term "non-pathogenic bacteria" refers to bacteria that do not cause disease in a subject of interest.

As used herein, the term "zoonotic infection" refers to an infection shared in nature by humans and other species of vertebrate animals. In contrast, the term non-zoonotic infection" refers to an infection that is not shared in nature by humans and other vertebrate animal species.

As used herein, the term "arthropod borne infection" refers to an infection that is transmitted to vertebrate animals (e.g., mammals including humans) by invertebrates of the phylum Arthropoda. In some embodiments, the arthropod is an insect such as a flea (e.g., transmits the Plague bacterium) or an arachnid such as a tick (e.g., transmits the Lyme disease bacterium).

The terms "N-terminus" "NH$_2$-terminus" and "amino-terminus" refer to the amino acid residue corresponding to the methionine encoded by the start codon (e.g., position or residue 1). In contrast the terms "C-terminus" "COOH-terminus" and "carboxy terminus" refer to the amino acid residue encoded by the final codon (e.g., last or final residue prior to the stop codon).

The term "antibody" refers to polyclonal and monoclonal antibodies. Polyclonal antibodies which are formed in the animal as the result of an immunological reaction against a protein of interest or a fragment thereof, can then be readily isolated from the blood using well-known methods and purified by column chromatography, for example. Monoclonal antibodies can also be prepared using known methods (See, Winter and Milstein, Nature, 349, 293-299, 1991). As used herein, the term "antibody" encompasses recombinantly prepared, and modified antibodies and antigen-binding fragments thereof, such as chimeric antibodies, humanized antibodies, multifunctional antibodies, bispecific or oligospecific antibodies, single-stranded antibodies and F(ab) or F(ab)$_2$ fragments. The term "reactive" when used in reference to an antibody indicates that the antibody is capable of binding an antigen of interest. For example, a OspA-reactive antibody binds to OspA or to a fragment of OspA.

The terms "auto-antibody" or "auto-antibodies" refer to any immunoglobulin that binds specifically to an antigen that is native to the host organism that produced the antibody (i.e., the antigen is not synthetic and/or has not been artificially supplied to the host organism). However, the term encompasses antibodies originally produced in response to the administration or presence of a foreign and/or synthetic substance in the host that also cross-react with "self" antigens. Exemplary auto-antibodies include, without limitation, anti-LFA1 antibodies.

The term "cytokine" refers to a molecule, such a protein or glycoprotein, involved in the regulation of cellular proliferation and function. Cytokines are exemplified by lymphokines (e.g., tumor necrosis factor-α, tumor necrosis factors, interferon-γ, etc.), growth-factors (e.g., erythropoietin, insulin, G-CSF, M-CSF, GM-CSF, EGF, PDGF, FGF, etc.), and interleukins (e.g., IL-2, IL-4, IL-5, IL-6, IL-9, IL-10, IL-13, etc.).

The term "B cell epitope" as used herein refers to an antigenic determinant (protein or carbohydrate) to which a single antibody molecule binds. B cell epitopes may comprise linear epitopes (amino acids adjacent to each other in the primary sequence) or conformational epitopes (moieties distant from each other in the primary sequence, but brought into close proximity of one another during folding of the antigen) of at least four amino acid residues.

The term "T cell epitope" as used herein refers to an antigenic determinant presented by a MHC class I or a MHC class II molecule, for binding by a single T cell receptor. T cell epitopes are linear epitopes comprising at least seven amino acid residues. In some embodiments of the present invention, the term T cell epitope comprises a T helper cell epitope, an antigen fragment presented by an MHC class II molecule for binding to T cell receptor on the surface of a helper T cell (e.g., generally CD4$^+$).

The term "conservative substitution" as used herein refers to a change that takes place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally grouped separately as aliphatic-hydroxyl; (4) aromatic (phenylalanine, tyrosine, tryptophan); (5) amide (asparagine, glutamine); and (6) sulfur-containing (cysteine and methionine). Whether a change in the amino acid sequence of a peptide results in a functional homolog can be readily determined by assessing the ability of the variant peptide to function in a fashion similar to the wild-type protein. Peptides having more than one replacement can readily be tested in the same manner. In contrast, the term "nonconservative substitution" refers to a change in which an amino acid from one family is replaced with an amino acid from another family (e.g., replacement of a glycine with a tryptophan). Guidance in determining which amino acid residues can be substituted, inserted, or deleted without abolishing biological activity can be found using computer programs (e.g., LASERGENE software, DNASTAR Inc., Madison, Wis.).

The terms "antigen," "immunogen," "antigenic," "immunogenic," "antigenically active," and "immunologically active" refer to any substance that is capable of inducing a specific humoral and/or cell-mediated immune response. An immunogen generally contains at least one epitope. Immunogens are exemplified by, but not restricted to molecules that contain a peptide, polysaccharide, nucleic acid sequence, and/or lipid. Complexes of peptides with lipids, polysaccharides, or with nucleic acid sequences are also contemplated, including (without limitatidn) glycopeptide, lipopeptide, glycolipid, etc. These complexes are particularly useful immunogens where smaller molecules with few epitopes do not stimulate a satisfactory immune response by themselves.

A peptide sequence and nucleotide sequence may be "endogenous" or "heterologous" (i.e., "foreign"). The term "endogenous" refers to a sequence naturally found in the cell or virus into which it is introduced so long as it does not contain some modification relative to the naturally occurring sequence. The term "heterologous" refers to a sequence that is not endogenous to the cell or virus into which it is introduced. For example, heterologous DNA includes a nucleotide sequence ligated to, or manipulated to become ligated to a nucleic acid sequence to which it is not ligated in nature, or to which it is ligated at a different chromosomal or extrachromasomal location in nature. Heterologous DNA also includes a nucleotide sequence naturally found in the cell or virus into which it is introduced and which contains some modification relative to the naturally occurring sequence. Generally, although not necessarily, heterologous DNA encodes heterologous RNA and heterologous proteins that are not normally produced by the cell or virus into which it is introduced. Examples of heterologous DNA include reporter genes, transcriptional and translational regulatory sequences, DNA sequences which encode selectable marker proteins (e.g., proteins which confer drug resistance), etc.

The terms "peptide," "peptide sequence," "amino acid sequence," "polypeptide," and "polypeptide sequence" are used interchangeably herein to refer to at least two amino acids or amino acid analogs, which are covalently linked by a peptide bond or an analog of a peptide bond. The term "peptide" includes oligomers and polymers of amino acids or amino acid analogs. The term "peptide" also includes molecules commonly referred to as peptides, which generally contain from about two (2) to about twenty (20) amino acids. The term "peptide" also includes molecules commonly referred to as polypeptides, which generally contain from about twenty (20) to about fifty amino acids (50). The term "peptide" also includes molecules commonly referred to as proteins, which generally contain from about fifty (50) to about three thousand (3000) amino acids. The amino acids of the peptide may be L-amino acids or D-amino acids. A peptide, polypeptide or protein may be synthetic, recombinant or naturally occurring. A synthetic peptide is a peptide produced by artificial means in vitro.

The terms "mammals" and "mammalian" refer to animals of the class mammalia, which nourish their young by fluid secreted from mammary glands of the mother, including human beings. The class "mammalian" includes placental animals, marsupial animals, and monotrematal animals. An exemplary "mammal" may be a rodent, primate (including simian and human) ovine, bovine, ruminant, lagomorph, porcine, caprine, equine, canine, feline, avian, etc. Preferred non-human animals are selected from the order Rodentia. Preferred embodiments of the present invention are primarily directed to vertebrate (backbone or notochord) members of the animal kingdom.

The terms "patient" and "subject" refer to a mammal that may be treated using the methods of the present invention.

The term "control" refers to subjects or samples which provide a basis for comparison for experimental subjects or samples. For instance, the use of control subjects or samples permits determinations to be made regarding the efficacy of experimental procedures. In some embodiments, the term "control subject" refers to a subject that receives a mock treatment (e.g., saline alone or OspA without a heterologous antigen insert or conjugate).

As used herein, the term "immune response" refers to the reactivity of an organism's immune system in response to an antigen. In vertebrates, this may involve antibody production, induction of cell-mediated immunity, and/or complement activation (e.g., phenomena associated with the vertebrate immune system's prevention and resolution of infection by microorganisms). In preferred embodiments, the term immune response encompasses but is not limited to one or more of a "lymphocyte proliferative response," a "cytokine response," and an "antibody response."

In particularly preferred embodiments, the immune response is largely reactive with an antigen of interest. For instance, when used in reference to administration of a hybrid OspA/C1 vaccine to a mammalian subject, the term refers to the immune response produced (or elevated) in the subject to the OspA and/or the OspC1 portions of the fusion protein. Immune responses reactive with an antigen of interest are measured in vitro using various methods disclosed herein.

The term "reactive with an antigen of interest" when made in reference to an immune response refers to an increased level of the immune; response to the antigen of interest as compared to the level of the immune response to control antigen. (e.g., unrelated antigen).

The term "lymphocyte proliferative response" refers to antigen-induced lymphocyte (e.g., PBL) increase in cell number. Alternatively, or in addition, the term "proliferation" refers to the physiological and morphological progression of changes that cells undergo when dividing, for instance including DNA replication as measured by tritiated thymidine incorporation.

The term "cytokine response" refers to antigen-induced cytokine secretion by lymphocytes as measured for instance by assaying culture supernatants for cytokine content (e.g., IL-2, IFNγ, TNFα, IL-4, etc) by ELISA.

The term "antibody response" refers to the production of antibodies (e.g., IgM, IgA, IgG) that bind to an antigen of interest, this response is measured for instance by assaying sera by antigen ELISA or western blot (serum antibody response). Similarly, a mucosal antibody response is measured for instance by assaying mucosal washes or secretions (e,g, bronchial lavage, urine, stool, saliva, tears, etc.) by antigen ELISA.

The term "adjuvant" as used herein refers to any compound which, when injected together with an antigen, non-specifically enhances the immune response to that antigen. Exemplary adjuvants include but are not limited to incomplete Freunds adjuvant (IFA), aluminum-based adjuvants (e.g., AIOH, AIPO4, etc), and Montanide ISA 720.

The terms "diluent" and "diluting agent" as used herein refer to agents used to diminish the strength of an admixture. Exemplary diluents include water, physiological saline solution, human serum albumin, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

The terms "carrier" and "vehicle" as used herein refer to usually inactive accessory substances into which a pharmaceutical substance (e.g., OspA vaccine) is suspended. Exemplary carriers include liquid carriers (such as water, saline, culture medium, saline, aqueous dextrose, and glycols) and solid carriers (such as carbohydrates exemplified by starch, glucose, lactose, sucrose, and dextrans, anti-oxidants exemplified by ascorbic acid and glutathione, and hydrolyzed proteins.

Brief Description of the Invention

The present invention provides an oral delivery system for vaccination of humans and other animals. For instance, the oral delivery system can either be deployed in the wild to vaccinate nonhuman vertebrate hosts of zoonotic bacteria, or be used directly in the clinic to vaccinate humans against zoonotic or non-zoonotic bacterial diseases. In some embodiments, the present invention provides an oral vaccine comprising *Escherichia coli* or *Lactobacillus plantarum* expressing *B. burgdorferi* OspA and/or OspC (e.g., Lyme disease vaccine). In some preferred embodiments, the oral vaccine is freeze dried. In additional embodiments, the oral vaccine comprises a recombinant nonpathogenic bacterial vector expressing an antigen from a pathogenic bacterial pathogen (e.g., *Yersinia pestis* IcrV and/or caf1 as a Plague vaccine).

Detailed Description of the Invention

The present invention relates to vaccines for reduction of bacterial infections in animal and human populations. Some preferred embodiments of the present invention relates to Lyme disease vaccines for reduction of *Borrelia burgdorferi* infections in mammals. The invention is set forth in detail in the following sections: 1) The Tick Vector *Ixodes* scapularis; II) Outer Surface Protein Antigens of *Borrelia burgdorferi*; m) Freeze Dried and Live Oral Vaccines Comprising a Bacterial Vector; IV) Oral Vaccination of Laboratory Mice; V) Baits and Baiting Systems; VI) Oral Vaccination of Wildlife; VII) Oral Vaccination of Human Subjects; and VIII) Antigens of Other Pathogenic Bacteria.

I. The Tick Vector *Ixodes scapularis*

*Ixodes scapularis* ticks have a two-year life cycle with four stages: egg, larva, nymph and adult (Anderson, Conn Med, 53:343-346, 1989). Although ticks feed on three different hosts during their lives (Bosler, *Lyme Disease*, Coyle (ed.), St Louis, Mo.: Mosby-Year Books, Inc., pp 18-26, 1993), ticks feed only once at each stage of development, thereby limiting the number of hosts a single tick can infect with *B. burgdorferi*. Subadults feed on at least 31 species of mammals from seven orders (Anderson, Ann NY Acad Sci, 539:180-191, 1988). For *B. burgdorferi* to maintain its zoonotic cycle between hosts and vector, it must be transmitted from an infected host (e.g., mouse) to a tick during the larval feeding, survive the molt to the nymphal stage, and be passed to a naïve vertebrate during the nymphal feeding (Lane et al., Annu Rev Entomol, 36:587-609, 1.991).

The timing during the year that each *I. scapularis* stage is actively seeking a bloodmeal is very important to the proliferation of *B. burgdorferi*. Female ticks feed and mate on a vertebrate host in the fall, lay eggs in early spring and die shortly thereafter. The larvae hatch, feed in late summer and molt to nymphs. The nymphs emerge the following late spring and early summer, feed, and molt to adults that summer to renew the cycle. The importance to *B. burgdorferi* is that nymphs feed about two months before the larvae from the next generation. The nymphs infect the young vertebrate hosts from the spring cohorts from which the larvae are then infected in late summer. Many of the most important reservoir hosts, such as white-footed mice, eastern chipmunks (*Tamias striatus*) and short-tailed shrews (*Blarina brevicauda*), live less than one year, and no host can pass *B. burgdorferi* to its offspring transplacentally (Mather et al., J Infect Dis, 164: 564-567, 1991). Thus, the continued existence of *B. burgdorferi* requires continual passage from vertebrate-to-tick-to-naïve vertebrate. It is contemplated that a vaccine that drastically reduces the prevalence of *B. burgdorferi* in vertebrates, such as mice and chipmunks, will indirectly reduce the incidence of Lyme disease in human populations exposed in endemic areas.

II. Outer Surface Protein Antigens of *Borrelia burgdorferi*

*B. burgdorferi* infection induces a humoral immune response against major lipoprotein components of the outer surface membrane (Schwan et al., Proc Natl Acad Sci USA, 92:2909-2913, 1995), including outer surface proteins (Osps), OspA and OspC. OspA has been extensively studied as a vaccine against Lyme disease (Fikrig et al., Science, 250:553-556, 1990; Fikrig et al., Infect Immun, 60:773-777, 1992; de Silva et al., J Exp Med, 183:271-275, 1996; and Steere et al., N Engl J Med, 339:209-215, 1998). OspA based vaccines work in a unique manner. Antibodies target spirochetes in the midgut of the tick vector blocking its transmission to the host. *B. burgdorferi* is eliminated from ticks that feed on OspA immunized mice, suggesting that the pathogen is destroyed within its vector (Fikrig et al., Proc Natl Acad Sci USA, 89:5418-5421, 1992; and Dunne et al., Infect Imun, 63:1611-1614, 1995). The inverse relationship between OspA and OspC in spirochetes during tick feeding led to the hypothesis that bacteria producing OspC invaded the salivary glands and entered the host (Piesman, J Infect Dis, 167:1082-1085, 1993; Schwan et al., supra, 1995, and de Silva et al., supra, 1996). According to the current hypothesis regarding *B. burgdorferi* gene expression in the tick, once the tick starts feeding, unknown signals induce the downregulation of ospA permitting the spirochete to detach from the midgut tissue (Pal et al., J Clin Invest, 106:561-569, 2000; and Pal et al., J Immunol, 166:7398-7403, 2001) and induce the upregulation of ospC, which is involved in the migration of the spirochete from the midgut to the salivary gland (Gilmore et al., Infect Imun, 68:411-414, 2000). However, once the feeding process starts, several spirochete populations are found in the midgut, including *B. burgdorferi* that express only OspA, only OspC, both OspA and OspC, and neither OspA nor OspC. These infectious spirochetes clear OspA en route to the salivary glands and then enter the host skin (Ohnishi et al., Proc Natl Acad Sci USA, 98:670-675, 2001). A burst of bacterial expression of OspC in the tick gut implies that the protein may facilitate or be necessary for the initial movement of the spirochetes through the tick hemocele. Consequently, antibodies that target OspC are thought to block the translocation of the microorganism from the gut to the salivary gland (Ohnishi et al., supra, 2001; and Anguita et al., FEMS Microbiol Rev, 27:493-504, 2003).

In addition, OspC remains actively expressed in *B. burgdorferi* in the vertebrate host for about ten days (Fingerle et al., J Clin Microbiol, 33:1867-1869, 1995), suggesting that OspC plays a role in establishment of infection in the vertebrate (Schwan et al., supra, 1995; and Stevenson et al., Infect Immun, 63:4535-4539, 1995). The serologic response to OspC by the mammalian immune system occurs early in infection and is very strong (Wilske et al., Infect Immun, 61:2182-2191, 1993; Jauris-Heipke et al, Med Microbiol Immunol (Berl), 82:37-50, 1993; and Stevenson et al., FEMS Microbiol Lett, 124:367-372, 1994). Moreover, OspC is a protective antigen against infection with cloned *B. burgdorferi* (Barthold, Infect Immun, 67:36-42, 1999; and Gilmore et al., Infect Immun, 64:2234-2239, 1996). The inventors contemplate that targeting both OspA and OspC in the tick gut, as well as targeting OspC in the host, would provide a vaccine with greater efficacy than the Lyme disease vaccines of the prior art.

OspC is one of the few loci in the *B. burgdorferi* genome that shows a high degree of polymorphism. More importantly, most of the variation found within the species can be found within each population (Jauris-Heipke et al., supra, 1993; and Wang et al., Genetics, 151:15-30, 1999). There are 22 different ospC major groups found worldwide in *B. burgdorferi* populations (Seinost et al., Infect Immun, 67:3518-3524, 1999; and Lin et al., J Clin Microbiol, 40:2572-2583, 2002). A major group is defined as a group of alleles that differ in more than eight percent of their sequences from other major groups (average difference of about 14%), and with less than two percent difference from members of the same group (average difference of less than 1%). *B. burgdorferi* has the greatest density and diversity in the northeastern part of the United States, with seventeen different ospC groups represented in this region (Qiu et al., Genetics, 160:833-849, 2002). Far fewer groups have been found in other areas of the world. In 132 patients from Long Island, 11 ospC serotypes were found in skin biopsies of the leading edge of the erythema migrans lesion at low frequencies, while four groups, A, B, I and K, made up the remaining 70%. These same four groups were the only ones found in patients with *B. burgdorferi* disseminated in the blood or spinal fluid (Seinost et al., supra, 1999).

A study in wild animals was recently conducted in New York, to determine the percentage of individuals from a species that are infected with a given OspC group. Of the four species tested (white-footed mouse, shrew, chipmunk and squirrel) two major OspC groups, OspC1 (group A) and OspC12 (group K) were consistently identified. As these two OspC groups are two of the major groups found in disseminated disease in humans, some preferred embodiments of the present invention provide vaccines with OspC antigens of groups A and K for both wildlife and human use. However, the present invention is not limited to OspC1 and OspC12. For instance, additional embodiments of the present invention provide vaccines with OspC antigens corresponding to other groups frequently detected in wildlife, such as OspC2 (group B, e.g., GENBANK Accession No. AF029861), OspC4 (group D, e.g.; GENBANK Accession No. AF029863), OspC6 (group F, e.g., GENBANK Accession No. AF029865), OspC8 (group G, e.g., GENBANK Accession No. AF029867), and/or OspC10 (group I, e.g., GENBANK Accession No. AF029869) all nucleic acid and amino acid sequences herein incorporated by reference.

In addition, a recombinant OspA lipoprotein has been produced that has the hLFA1 cross-reactive epitope mutated (OspAhLFA). This epitope has been described as a factor in autoimmune arthritic responses against OspA (Gross et al., Science, 281:703-706, 1998). By eliminating this epitope, the risk of potential adverse side effects from a native OspA based human vaccine is reduced. In preliminary studies, this mutated OspA lipoprotein was shown to be as good a vaccine candidate against challenge with *B. burgdorferi* infected field ticks, as the native OspA lipoprotein. A *Lactobacillus plantarum* strain expressing the HLFA1-mutated OspA lipoprotein (OspAhLFA) is produced in a similar manner. This immunogen is tested as a potential oral vaccine candidate against Lyme disease for human use, as described below.

Further embodiments of the present invention comprise chimeric outer surface proteins. For instance, the present invention provides vaccines including one or more of OspA, OspC1, and OspC12, as well as chimeric fusion proteins such as one or more of OspA/C1, OspA/C12, OspC1/A, OspC1/C12, OspC12/A, and OspC12/C1. In additional embodiments, the vaccine antigen is a mosaic protein of three or more bacterial antigens (e.g., OspB/C1/C12). Exemplary Lyme disease Osp sequences are shown below in Table 1.

TABLE 1

Exemplary *B. burgdorferi* Antigen Sequences

| Antigen | Sequence Identifier | Description |
| --- | --- | --- |
| OspA | SEQ ID NO: 2 | Lipidated OspA |
| OspC1 | SEQ ID NO: 4 | Lipidated OspC1 |
| OspC12 | SEQ ID NO: 6 | Lipidated OspC12 |
| OspA- | SEQ ID N0: 7 | Lipidated OspA mutant |
| OspC1/A | SEQ ID NO: 8 | Lipidated OspC1/A |
| OspC1/A-ΔLFA | SEQ ID NO: 9 | Lipidated OspC1/A mutant |
| uOspC1/A | SEQ ID NO: 10 | Unlipidated OspC1/A |
| uOspC1/A-ΔLFA | SEQ ID NO: 11 | Unlipidated OspC1/A mutant |
| OspB/C1/C12 | SEQ ID NO: 12 | Lipidated OspC1/C12 |
| uOspC1/C12 | SEQ ID NO: 13 | Unlipidated OspC1/C12 |
| OspC12/A | SEQ ID NO: 14 | Lipdated OspC12/A |
| OspC12/A- | SEQ ID NO: 15 | Lipidated OspC12/A mutant |
| uOspC12/A | SEQ ID NO: 16 | Unlipidated OspC12/A |
| uOspC12/A- | SEQ ID NO: 17 | Unlipidated OspC12A mutant |

III. Freeze Dried and Live Oral Vaccines Comprising a Bacterial Vector

Oral immunization is an attractive means for vaccine administration because it is noninvasive and because it is suitable for economic mass vaccination campaigns. There is a precedent for the development of vaccines to disrupt the enzootic transmission cycle of *B. burgdorferi*. Fikrig and colleagues found that mice inoculated orally with a suspension of *E. coli* freshly induced for expression of OspA, were protected from needle challenge with *B. burgdorferi* (Fikrig et al., J Infect Dis, 164:1224-1227, 1991). It was later found that OspA lipoprotein of *B. burgdorferi* is a mucosal immunogen and adjuvant (Erdile and Guy, Vaccine, 15:988-996, 1997) and that oral delivery of purified OspA lipoprotein protects mice from systemic infection with *B. burgdorferi* (Luke et al., Vaccine, 15:739-746, 1997). More recently, OspA needle immunization was shown to decrease transmission of *B. burgdorferi* from infected white-footed mice to larval L scapularis ticks (Tsao et al, Vector Borne Zoonotic Dis, 1:65-74, 2001). However, delivering vaccines as subcutaneous inoculations in the wild is impractical. Thus what is needed in the art is an oral vaccine comprising OspA, for distribution as bait to wild mice and other *B. burgdorferi* reservoirs. As described herein, the inventors have made this approach feasible by development of a delivery vehicle for OspA and/or OspC immunogens. The delivery vehicle of the present invention permits packaging of the immunogen by a method suitable for ease of storage and distribution in the wild, but which withstands the elements (e.g., temperature, precipitation, etc.) without losing its immunogenicity.

Briefly, the inventors have succeeded in freeze-drying bacteria expressing recombinant *B. burgdorferi* OspA for use as an oral Lyme disease vaccine. In proof of concept studies, the freeze-dried powder was suspended in media and inoculated orally to mice susceptible to Lyme disease. All mice that developed a robust systemic antibody (IgG) response to OspA were protected against subsequent *B. burgdorferi* infection. Infection was shown by dark field microscopy of the cultures of the heart after 2 and 5 weeks, with subsequent confirmation by OspA nested PCR, and by western blot of the mouse sera obtained at termination. This is the first time that freeze-dried *E. coli* expressing OspA has been used to deliver an immunogen via the oral route to prevent Lyme borreliosis. This outcome was not predictable from studies of parenteral Lyme disease vaccines, as it had been previously shown in another system that while intraperitoneal administration of a *Fusobacterium necrophum* vaccine resulted in a protection rate of about 55%, oral administration of a lyophilized vaccine simply delayed time to death post challenge (Abe et al., Am J Vet Res, 39:115-118, 1978).

Freeze-drying is an excellent method to preserve bacteria for long periods of time. Freeze-dried *E. coli* expressing OspA provides an efficient oral delivery vehicle because the powder obtained can easily be made into pills or pellets for mixture with mouse feed. Packaging of this immunogen into other formats, which would resist the elements (e.g., temperature, humidity, etc.) in the wild for a period of several months, is also contemplated (e.g., paraffinized pellets).

It has long been recognized that the feeding of soluble proteins can result in a state of immunological non-responsiveness termed oral tolerance (Strobel et al., Immunology, 49:451-456, 1983; and Mowat et al., Immunology, 56:253-260, 985). Observations to date have underlined the superiority of live vaccines (e.g., attenuated pathogenic viruses and bacteria) over non-replicating vaccines antigens (e.g., peptides, purified proteins, killed microbes) for the induction of mucosal immune responses. However, potential safety and environmental considerations discourage employment of the majority of mucosally delivered vectors, such as *E. coli, Salmonella* and Vaccinia virus (Shaw et al., Immunology, 100:510-518, 2000).

In contrast, the "generally recognized as safe" status of dietary lactic acid bacteria, such as *Lactobacillus* spp., render them particularly attractive as mucosal vaccine carriers. Specific *Lactobacillus* strains are also reputed to exert beneficial health properties and have been intensively studied as part of probiotic applications (Reveneau et al., Vaccine, 20:1769-1777, 2002). Lactobacilli bacteria maintain a sophisticated, non-invasive ecology within the host and their capacity to enhance immune responses or natural immuno-adjuvanticity has been demonstrated (Gerritse et al., Res Microbiol, 141: 955-962, 1990; Perdigon et al., J Dairy Res, 58:485-496, 1991; Link-Amster et al., FEMS Immunol Med Microbiol, 10:55-63, 1994; Isolauri et al., Vaccine, 13:310-312, 1995; and Pouwels et al., J Biotechnol, 44:183-192, 1996). This is likely the result of the macrophage-activating and interferon-γ (IFN-γ)-inducing properties of the grain-positive peptidoglycan (Rangavajhyala et al., Nutr Cancer, 28:130-134, 1997) and lipoteichoic acid fractions (Suda et al., FEMS Immunol Med Microbiol, 12:97-112, 1995). Expression vectors have been designed for *Lactobacillus* spp., for targeted delivery of antigens, and *Lactobacillus* spp. have been shown to be functional as humoral and mucosal antigen carriers (Maassen et al., Vaccine, 17:2117-2128, 1999; Pavlova et al., Plasmid, 47:182-192, 2002; Scheppler et al., Vaccine, 20: 2913-2920, 2002; and Grangette et al., Vaccine, 20:3304-3309, 2002).

As described herein, the exemplary non-pathogenic, food grade bacterium, *Lactobacillus plantarum*, was developed as an alternative vehicle for oral delivery of a *B. burgdorferi* vaccine to wildlife, and as a preferred vehicle for oral delivery of a *B. burgdorferi* vaccine to humans. However, the present invention is not limited to this species or strain of *lactobacillus*. In fact, other species including but not limited to *L. acidophilus, L. brevis, L. casei, L. crispatus, L. fermentum, L. gasseri, L. reuteri, L. rhamnosus*, and *L. salivarius*, are also contemplated to be suitable for use in vaccine compositions.

A *Lactobacillus plantarum* strain expressing OspA and a chimera of OspC and OspA was successfully constructed. The strain used for the initial proof of concept experiments was *L. plantarum* 256 (See, e.g., WO 01/21200, herein incorporated by reference in its entirety). The *Lactobacillus* clones are then freeze-dried and tested in mice. It is contemplated that a vaccine based on freeze-dried *Lactobacillus* expressing OspA and OspC is suitable for use as a one-dose vaccine since freeze drying does not kill the organisms, permitting their colonization of the gastrointestinal tract for prolonged exposure to the immune system.

Figure 2:
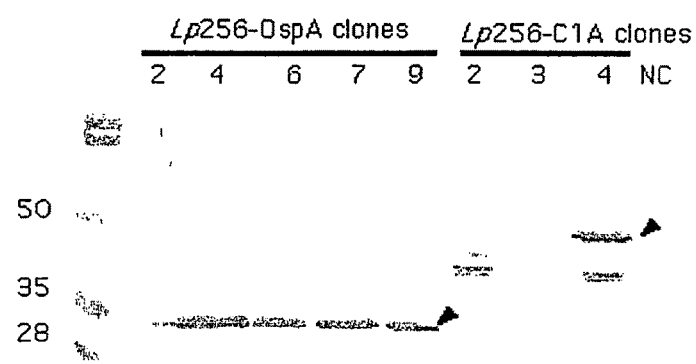
FIG. 2 show's a western blot of *Lactobacillus plantarum* strain 256 (LP256) expressing *B. burgdorferi* OspA (Lp-A, 31 Kd), and LP256 expressing a fusion protein of OspC1 and OspA (Lp-C1A, 53 Kd) with NC designating the negative control. The blot was probed with a combination of anti-OspC (mAb 3.8) and anti-OspA (mAbs LA2.2 and 336.1) antibodies.
Figure 3:
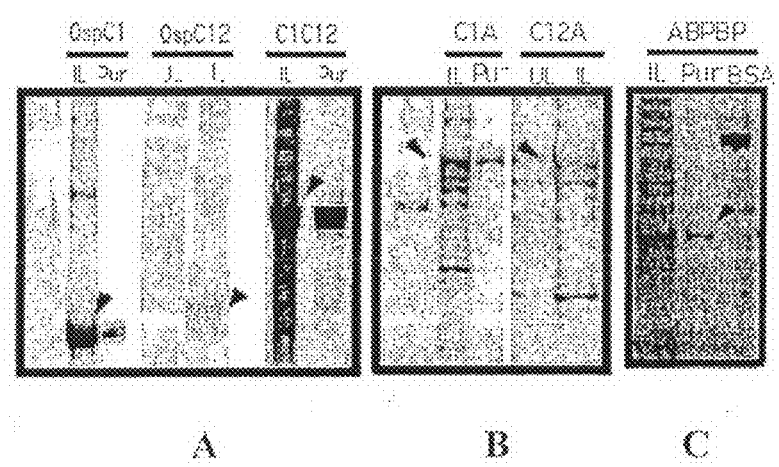
FIG. 3 depicts the expression of various *B. burgdorferi* OspC antigens by transformed *E. coli*, as visualized on Coomassie stained SDS-PAGE gels. Panel A shows bacterially expressed OspC1 (22 Kd), OspC12 (22 Kd), and an OspC1/OspC12 chimera, C1C12 (44 Kd). Panel B shows bacterially expressed OspC/OspA chimeras, C1A and C12A (53 Kd). Panel C shows bacterially expressed OspAhLFA–. Abbreviations are as follows: IL, induced lysate; Pur, purified; UL, uninduced lysate; and BSA, bovine serum albumin.

Multiple *B. burgdorferi* ospA and ospC genes have been cloned and protein has been induced in *E. coli* BL21(DE3): single genes, OspA, hLFA1 mutated OspA (OspAhLFA⁻), OspC1, OspC12; and chimeras between two different genes, C1.C12, C1.A, C12.A, C1.AhLFA⁺, C12.AhLFA⁻ (See, FIGS. 1 and 3). In addition, several *B. burgdorferi* ospA and ospC genes have been cloned and protein has been induced in *L. plantarum* strain 256: OspA, and C1.AhLFA– (See, FIG. 2).

After protein induction, *E. coli* expressing these antigens (Ec-A, Ec-AhLFA⁻, Ec-C1, Ec-C12, Ec-C1.C12, Ec-C1.A, Ec-C12.A, Ec-C1.AhLFA⁻, and Ec-C12.AhLFA⁻) are lyophilized (freeze-dried as described in Example 1). The same *B. burgdorferi* immunogens are cloned in *L. plantarum*, strain 256 (Lp-A, Lp-AhLFA⁻, Lp-C1, Lp-C12, Lp-C1.C12, Lp-C12.A, Lp-C1.AhLFA⁻, and Lp-C12.AhLFA⁻). Similarly, after protein induction the *L. plantarum* 256-based Lyme disease vaccines are lyophilized, following the protocol used for *E. coli*. This protocol is expected to be applicable to *Lactobacillus* spp., since freeze-drying *Lactobacillus* strains has been previously reported (King et al., J Gen Appl Microbiol, 44:160-165, 1998; and Prasad et al., Appl Environ Microbiol, 69:917-925, 2003). Viability of lyophilized *E. coli* and *L. plantarum* is checked by plating out serial dilutions of freeze-dried powder re-suspended in pre-warmed culture media (e.g., LB, TBY, etc.) and then counting the colonies obtained the following morning. The antigenicity of the proteins expressed by freeze-dried *E. coli* and *L. plantarum* is checked by western blot using anti-OspA (e.g., mAbs LA2 and 336 which bind to the protective C-terminal of OspA) and anti-OspC mAbs as described in Example 4.

IV. Oral Vaccination of Laboratory Mice

Figure 4:
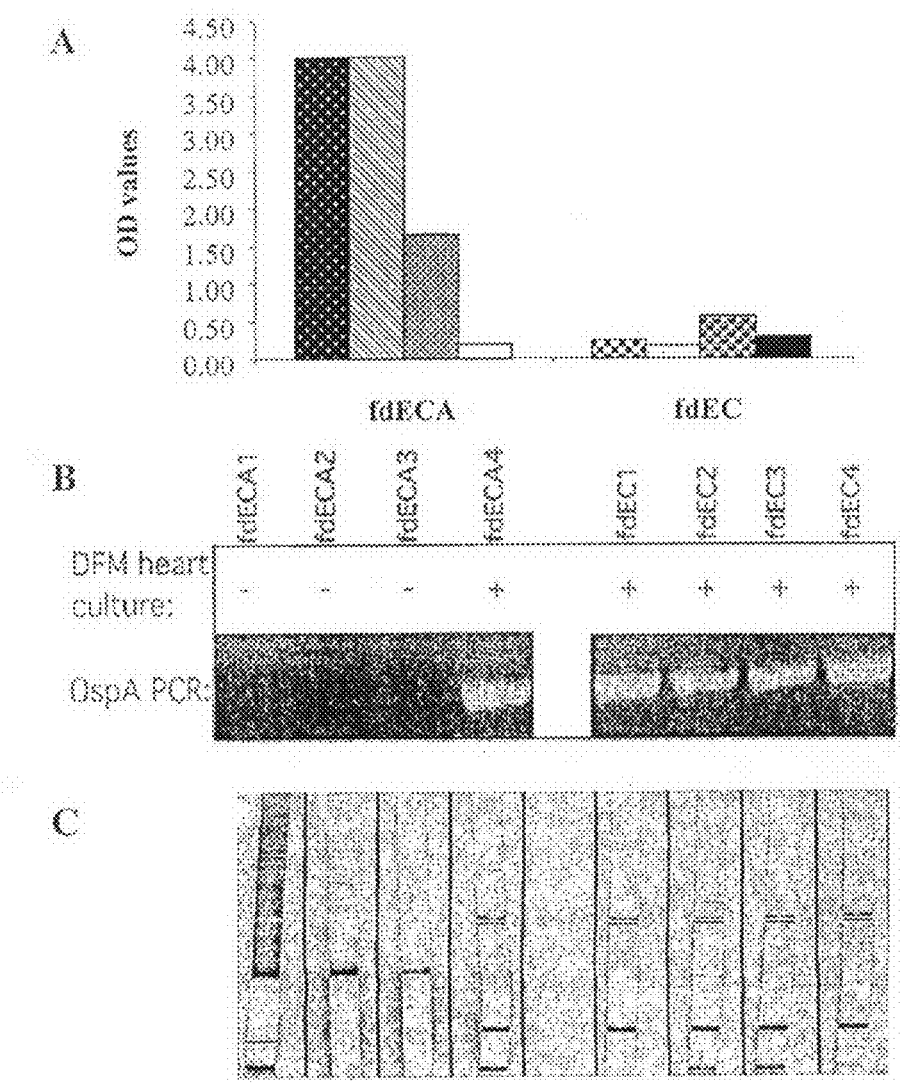
FIG. 4 illustrates the correlation between anti-OspA serum titer and protection against *B. Burgdorferi* infection in mice orally vaccinated with freeze-dried *E. coli* (fdEC) expressing *B. burgdorferi* OspA. Panel A provides OspA-ELISA OD values of sera from mice immunized by oral gavage (fdECA, freeze dried *E. coli* expressing OspA; and fdEC, freeze dried *E. coli*) two days prior to *B. burgdorferi* challenge (day 25). Panel A provides the results of dark field microscopy (DFM) analysis of heart cultures harvested 2 weeks after *B. burgdorferi* challenge (day 41), and read two and five weeks later. Culture results were confirmed by OspA nested PCR. Panel C shows a western blot analysis sera (IgG) obtained from immunized mice at termination (day 41). Mice that developed an IgG response to the oral vaccine were protected from infection two weeks after challenge with *B. burgdorferi*.
Figure 5:
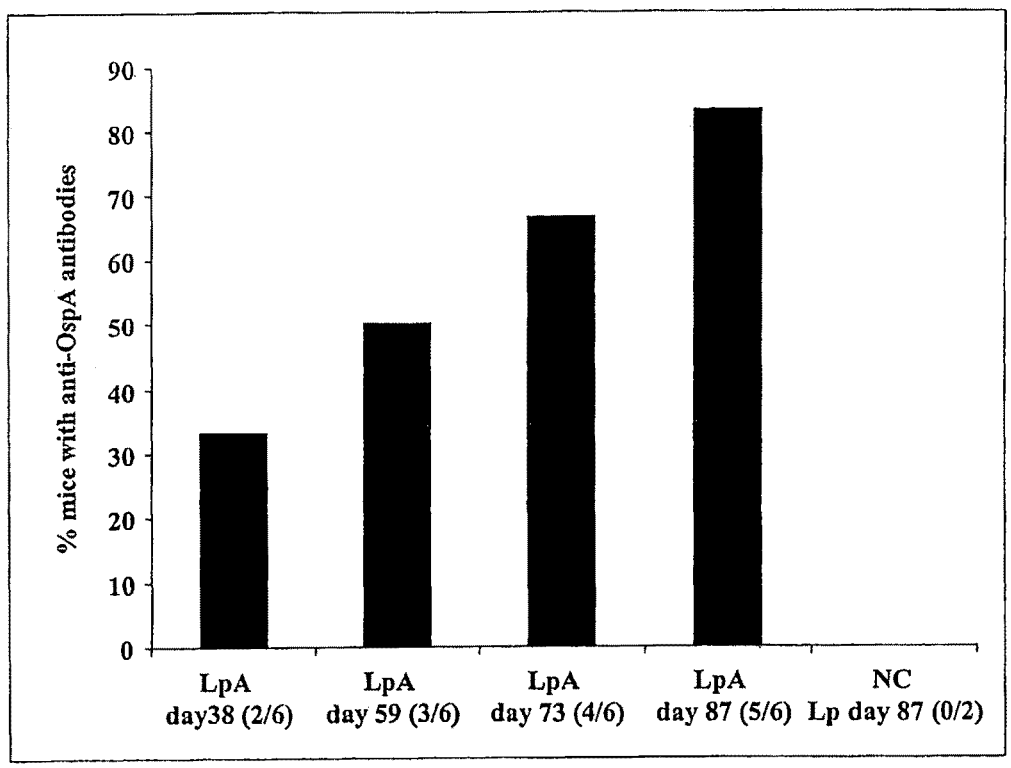
FIG. 5 shows the percentage of mice that developed systemic IgG antibodies against *B. burgdorferi* OspA after oral immunization with live *Lactobacillus plantarum* 256 expressing OspA.

Vaccine candidates are tested in Lyme disease susceptible mice (strain C3H-HeJ) by oral gavage inoculation of suspensions made after freeze-drying *E. coli* or *L. plantarum* expressing *B. burgdorferi* antigens. The immunogens are inoculated as a cocktail of freeze-dried bacteria expressing two independent proteins including OspA and OspC epitopes at a 1:1 ratio. Since several different recombinant antigens are produced, multiple combinations are possible. These are compared with freeze-dried *E. coli* expressing OspA (Ec-A), which is documented herein to be a good vaccine candidate (See, FIG. 4). Induced, vectorless, *E. coli* or *L. plantarum* are used as negative controls. Combinations to be tested as wildlife vaccine candidates include but are not limited to: *E. coli* and *L. plantarum* (vehicles) expressing OspC1.C12 plus OspA, OspC1 plus OspC12.A, and OspC12 plus OspC1.A (antigens). The following groups of mice are examined: (2 vehicles×3 antigens) 6 *B. burgdorferi* vaccines plus 3 control vaccines (positive control Ec-A, negative control Ec and negative control Lp)=9 groups. Combinations to be tested as human vaccine candidates include but are not limited to: *L. plantarum* expressing OspC1.C12 plus OspAhLFA⁻, OspC1 plus OspC12-AhLFA⁻, and OspC12 plus OspC1.AhLFA⁻. The following groups of mice are examined: (1 vehicle×3 antigens) 3 *B. burgdorferi* vaccines plus 1 positive control vaccine (Ec-A) plus 1 negative control vaccine (Lp)=5 groups. A total of 14 groups of mice (5 mice per group) are tested by oral gavage/needle challenge (See, Examples 6).

Protection is assessed two weeks after needle challenge with cultured *B. burgdorferi* B31. Briefly, heart tissue from mice is cultured, and nested PCR reactions are conducted on the same culture material. In addition, PCR on samples of ear tissue is done to assess possible bacterial dissemination, and western blots of sera are completed. Furthermore, neutralization assays are done with sera from vaccinated mice and different strains of *B. burgdorferi*, to assess the immunogenicity of the oral vaccines. Sera used in these experiments are obtained 2 weeks after the last boost, In vitro growth inhibitory activity of mouse sera is also assessed using methods based on published reports (Sadziene et al., J Infect Dis, 167:165-172, 1993, Johnson et al., Vaccine, 13:1086-1094, 1995; and Luke et al., Vaccine, 15:739-746, 1997) and as described in Example 10. In addition, LA2 equivalent antibody titers in sera are measured by mAbLA2.2 competition ELISA as described in Example 11, since this type of humoral immune response was found to be associated with inhibition of *B. burgdorferi* in vitro, and protection of hamsters from infection in vivo (Johnson et al., supra, 1995). The best vaccine candidates are then tested in tick challenge studies.

The ability of the oral vaccines to block transmission of the spirochete in the gut of the tick vector, when the infected tick vector (*Ixodes* nymph) feeds on the vaccinated mammalian host is also assessed. This property has been demonstrated for mice vaccinated parenterally with a solution of OspA lipoprotein, and subsequent challenge with infected nymphs (Fikrig et al., Proc Natl Acad Sci USA, 89:5418-5421, 1992; and de Silva et al., J Exp Med, 183:271-275, 1996). For this investigation, mice are immunized with a suspension of $2 \times 10^8$ freeze-dried *E. coli* (or *L. plantarum*) expressing OspA and OspC, by oral gavage inoculation. For wildlife vaccines the following groups of mice are tested: (2 vehicles×1 antigen) 2 *B. burgdorferi* vaccines plus 1 positive control vaccine (Ec-A) plus 2 negative control vaccines (Ec and Lp)=5 groups. For human vaccines the following groups of mice are tested: (1 vehicle×1 antigen) 1 *B. burgdorferi* vaccine plus 1 positive control vaccine (Ec-A) plus 1 negative control vaccine (Lp)=3 groups. Thus, a total of 8 groups of mice are tested by oral gavage/nymph challenge (See, Example 8).

In addition, the ability of circulating anti-OspA and anti-OspC antibodies to block spirochete transmission from the infected vaccinated mammalian host (mouse) to the uninfected vector (*Ixodes* larva) is assessed. Conventional immunization methods employing an OspA vaccine have previously been shown to decrease transmission of *B. burgdorferi* spirochetes from infected *Peromyscus leucopus* (white footed-mouse) to larval *Ixodes scapularis* ticks (Tsao et al., Vector Borne Zoonotic Dis, 1:65-74, 2001). For this investigation, mice are infected by intradermal injection of $2\times10^3$ *B. burgdorferi* B31 spirochetes (day 1): Infection is checked by western blot analysis of the sera obtained 10 days later, and by PCR of ear punch biopsies. Two weeks after *B. burgdorferi* infection (day 14), $2\times10^8$ *E. coli* (or *L. plantarum*) expressing immunogens are inoculated in a 250 μl volume by oral gavage inoculation for five consecutive days (day 14, 15, 16, 17, 18). The same vaccine candidates tested by oral gavage/nymph challenge are used. A total of 8 groups of mice are tested by oral gavage/larva challenge. Three days later, a 1st round of boosts are performed (day 21, 22, 23, 24, 25). Two weeks after the last boost (day 40), mice are infested with clean *Ixodes scapularis* larva to assess spirochete transmission to the uninfected tick. *Ixodes* ticks are collected after feeding on the infected/vaccinated mice for five days (days 41-45), after which mice are sacrificed. Blood and tissues are obtained to assess bacterial dissemination by culture of the heart, followed by confirmation by nested PCR of the same culture and by PCR of the ear tissue. OspA PCR of larva homogenates is done to determine spirochete transmission from the infected/vaccinated mouse to the uninfected tick (See, Example 12).

Lastly, the vaccine candidates that induce an immune response which blocks transmission of *B. burgdorferi* from the infected vaccinated mammalian host are examined to determine whether this blockage involves a total or a partial clearing of the spirochete from the host. This is accomplished by real-time PCR of the mouse ear, heart, joint and bladder, after the infection/vaccination protocol described above. Immunization of infected mice is done with *E. coli* and *L. plantarum* expressing *B. burgdorferi* OspA and OspC by oral gavage. The same vaccine candidates tested by oral gavage/larva challenge are examined. A total of 8 groups of mice are tested. Real time PCR of mouse tissue is done as known in the art (Wang et al., J Infect Dis, 186:782-791, 2002).

In an exemplary embodiment, freeze-dried *E. coli* BL21 (DE3) expressing OspA (Ec-A) was tested as a putative oral vaccine candidate in mice susceptible to Lyme disease (strain C3H-HeJ). Freeze-dried *E. coli* BL21 (DE3) lacking the OspA construct (Ec) was used as a negative control. Mice were immunized on day 1, 2, 3 and boosted on days 8, 9, 10 by oral gavage inoculation using disposable ball-tipped needles (Popper and Son). Two weeks later (day 25) mice were bled and seroconversion was tested by OspA-ELISA (1:100 dilution). Two days later (day 27) mice were needle challenged (subcutaneously) with $2\times10^3$ *B. burgdorferi*. Two weeks later (day 41), mice were sacrificed, and blood was collected to check protection by western blot and heart culture. Cultures were examined at 2 and 5 weeks, and 500 μl of culture material was collected to confirm the microscopy results with OspA PCR. By western blot only antibodies against OspA were identified in sera from immunized mice, indicating that the mice were protected from *B. burgdorferi* challenge (See, FIG. 4). In contrast, antibodies against several *B. burgdorferi* antigens were detected in the sera from control mice, indicating that the mice were infected by *B. burgdorferi*. Interestingly, one mouse immunized with freeze-dried *E. coli* expressing OspA (fdEc-A3) had considerably less antibody (lower OspA titer) than other immunized mice (fdEc-A1 and fdEc-A2) as determined by ELISA and western blot. However, all three mice were protected from *B. burgdorferi* infection. Protection of fdEc-A1, fdEc-A2 and fdEc-A3 was confirmed by negative culture of the heart and by negative PCR of this same material. One mouse immunized with oral freeze-dried *E. coli* expressing OspA, mouse number 4 (fdEc-A4) did not develop an appreciable antibody response to OspA. This mouse was not protected from *B. burgdorferi* infection, as determined by western blot and by positive culture of the heart. All negative control mice that had been immunized orally with a suspension of freeze-dried *E. coli* lacking the OspA construct (fdEc1, 2, 3, 4) were infected two weeks after challenge as seen determined by western blot and by positive culture of the hearts.

V. Baits and Baiting Systems

The bulk of the work on baits and baiting systems has been done for delivery of rabies vaccines (Pastoer et al., Vet Rec, 123:481-483, 1988; Knobel et al., J Wildl Dis, 38:352-362, 2002; and Estrada et al., BMC Infect Dis, 1:23, 2001). Plague vaccines (Creekmore et al., J Wildl Dis, 38:32-39, 2002) and immunocontraceptive vaccines (Bradley et al., Reprod Fertil Dev, 9:111-116, 1997) have also been delivered using baiting systems. However, to date no bait or baiting system has been developed for the delivery of a vaccine to prevent Lyme borreliosis in small vertebrates. A bait vaccine must contain a biomarker that allows for determination of the bait acceptance rate. Common biomarkers include rhodamine B, sulfadimethoxine (Southey et al., J Wildl Dis, 38:378-384, 2002), DuPont Blue dye, iophenoxic acid, and tetracycline hydrochloride (Fletcher et al., J Wildl Dis, 26:502-510, 1990; and Creekmore et al., supra, 2002). Baiting systems are usually developed to identify bait preference and bait acceptance rates for delivering an oral vaccine.

A baiting system is developed as described herein, in the laboratory by feeding mice susceptible to Lyme disease (C3H-HeJ) their regular chow admixed with pelleted freeze-dried *E. coli* (and *L. plantarum*) expressing *B. burgdorferi* immunogens, which have already been shown to be effective in preliminary oral gavage experiments. Mouse chow mixed with ground sunflower seed (to increase attractiveness) is provided together with the freeze-dried immunogen as bait. In the field, this bait is protected from the elements inside traps that are covered by boards. A unique advantage of developing a bait vaccine for small-rodent reservoirs is that, ultimately, a vaccine can be deployed in small, sealed containers with openings that will allow access only by small rodents and shrews (target species). In field trials the vaccine is deployed in live traps, which permits the simultaneous delivery of bait vaccine exclusively to target animals, the gathering of demographic data, and the assessment of bait consumption. However, the present invention is not limited to methods and systems for selective vaccine administration. For instance, alternative embodiments of the invention comprise methods and systems for broad vaccine delivery (e.g., crop dusting, seeding, fertilization, etc.).

Bait that needs to last for several months typically includes paraffin to reduce decomposition. The bait used in exemplary studies is not paraffinized, since trapping is done only 2-3 nights per week. The chow is admixed with the biomarker Rhodamine B, which is readily detectable by fluorescence microscopy of hair samples throughout the period of study (Southey et al., supra, 2002). This biomarker is used to determine the acceptance rate of the vaccine. Bait preference is tested later in the field studies, by comparing a first bait developed in the laboratory mouse model (mouse chow plus pelleted immunogen and Rhodamine B) to a second bait (mouse chow mixed with ground sunflower seeds plus pelleted immunogen and Rhodamine B). Since the bait is delivered in a pelleted immunogen, the bait acceptance rate can be checked, by observing how much of the pellet has been ingested.

The two best wildlife vaccine candidates (one in *E. coli* and one in *L. plantarum*) are made into freeze-dried pellets and fed to mice to test this mode of distribution as a bait vaccine.

These vaccines are admixed with a biomarker such as Rhodamine B that allows for determination of bait acceptance rate. Hair samples are obtained and analyzed by fluorescence microscopy throughout the period of study. Animals that ingested the freeze-dried pellet immunogen (or putative bait) have fluorescent hair. Immunization is done using the same schedule used for oral gavage inoculation. One group of mice is deprived of its regular mouse chow overnight and fed the immunogenic freeze-dried pellets the following day. Additionally, three other groups of mice are fed regular mouse chow, crimped oats, and crimped oats with sunflower seeds respectively, mixed with immunogenic freeze-dried pellets (containing rhodamine B) during the same time period. A control group of mice is fed regular chow without immunogenic pellets. Mouse hair is obtained to verify bait acceptance after oral immunization is finished. An initial experiment is done with a needle challenge. Other experiments including orally challenging vaccinated mice with infected ticks (nymphs) follow the initial trials. The following groups of mice are used: 2 *B. burgdorferi* vaccines×5 groups=10 groups×2 needle/nymph challenge=20 groups total. Protection is assessed as described in Section IV above.

If it is deemed desirable to increase oral vaccine efficacy, additional freeze-dried vaccines are made and tested as bait. For instance, vaccines with different ratios of OspC to OspA are formulated. Furthermore, *B. burgdorferi* OspC4, OspC6 and OspC8 have been cloned into *E. coli* and are ready for induction. These OspCs are contemplated to be useful, since they have been isolated at high percentages from mice and chipmunks, the main *B. burgdorferi* reservoirs.

Alternatively, oral wildlife vaccine candidates comprising the cholera toxin B subunit (CTB) as an adjuvant are produced. CTB is a potent mucosal adjuvant that induces both local and systemic immunity when delivered by the oral route. The adjuvant effect requires that antigen and toxin be administered simultaneously. For this reason, chimeras between OspA and CTB are also produced for expression in *E. coli*. Mice are highly resistant to cholera toxin and thus no problems arising from its toxicity are expected. In one embodiment, OspA is cloned at the N-terminus of pCTA2B (or pCTdeltaA1). This plasmid has been previously used successfully to generate a chimeric protein containing CTB (Hajishengallis et al., J Immunol, 154:4322-4332, 1995), and it has been kindly provided by Michael Russell from the University of Buffalo. CTB reagents for use in ELISA and western blots to measure chimeric protein expression are commercially available. Purified CTB is available from List Biologicals Laboratory, Inc. (Campbell, Calif.), and anti-CTB mAb is available from Maine Biotechnology Services, Inc. (Portland, Me.). In the event that CTB greatly improves the efficacy of *E. coli*-based Lyme disease vaccines, than similar *L. plantarum* based vaccines are constructed.

Animals without adequate antibody response are removed from the study by euthanasia. No problems are expected to arise from feeding *Lactobacillus* spp. to mice, since freeze-dried *Lactobacillus* strains have been previously fed to rats to reduce intestinal tumors (McIntosh et al., Nutr Cancer, 35:153-159, 1999; and Balansky et al., Cancer Lett, 147:125-137, 1999).

VI. Oral Vaccination of Wildlife

There is a strong positive correlation between human Lyme cases and the abundance of infected nymphal *I. scapularis* (Barbour and Fish, Science, 260:1610-1616, 1993; and Ostfeld and Keesing, Trends Ecol Evol, 15:232-237, 2000). Geographic comparisons (e.g., northeastern versus southeastern United States) strongly suggest that the infection prevalence percentage infected) in the nymphal *I. scapularis* population is correlated with risk of human exposure (LoGiudice et al., Proc Natl Acad Sci USA, 100:567-571, 2003). White-footed mice (*P. leucopus*) are considered the primary reservoir host for *B. burgdorferi* because they have a high reservoir competence (~90% of the larval ticks that feed on infected *P. leucopus* become infected), creating a high prevalence of infection in the tick population (Ostfeld et al., Vector Borne Zoonotic Dis, 1:55-63, 2001). These studies have also shown that the Eastern chipmunk (*Tamias striatus*) is a competent reservoir (~55% of larval ticks acquiring infection), but that all other mammalian hosts have substantially lower reservoir competence. It is contemplated that reducing the number of infected *P. leucopus* (and secondarily infected *T. striatus*) should lead to a decrease in the infection prevalence in the area and consequently a reduction in the incidence of human Lyme cases.

To assess the applicability of an oral wildlife vaccine for reducing the risk of Lyme disease to humans, the vaccines of the present invention are tested in a highly endemic natural setting. Field delivery of vaccine is targeted at mice and chipmunks. The Institute of Ecosystem Studies (IES) is a 980 hectare second growth forest with several surrounding human communities in Dutchess County, New York, which is representative of much of the northeastern United States. In fact, Dutchess County has one of the highest incidence rates (~600/100,000 population) and prevalence rates (up to 1,836 cases per annum) of Lyme disease of any county in the United States. Long-term data sets on natural reservoir hosts and *B. burgdorferi* have been collected there since 1991 and are available for comparison. At IES, both the cost of distributing the vaccine to mice and its efficacy in reducing the prevalence of infected *I. Scapularis* is determined.

A major goal for the oral wildlife vaccine is to reduce human exposure to ticks infected with *B. burgdorferi*, and therefore to reduce the incidence of Lyme disease in humans. Bait vaccines of the present invention are contemplated to provide a means to meet this goal by: (1) protecting free-ranging populations of white-footed mice and eastern chipmunks (the principal reservoir hosts for Lyme disease) from infection with *B. burgdorferi*; and (2) reducing the prevalence of *B. burgdorferi*-infected nymphal *I. scapularis*.

On the grounds of IES, populations of white-footed mice, Eastern chipmunks, and blacklegged ticks have been monitored for 12 years. All nine plots currently under study are available for testing the vaccines of the current invention, with four plots as control groups (no manipulations) and five plots as experimental groups (manipulations). The plots comprise similar oak-dominated forests and understory vegetation, as well as physical characteristics such as slope and drainage. Population dynamics of rodents within the nine plots have been synchronous over the past 5 years, indicating that they can realistically be considered as replicates. The plots are approximately 2.25 ha and consist of an 11 by 11 grid of trapping stations, with 15 meters between stations and two Sherman live-traps per station (for a total of 121 trap stations and 242 traps per grid). Each year from April through November, each grid is trapped for 2-3 consecutive nights every 3-5 weeks. This trapping regime results in capture probabilities of ~85%, where capture probability is defined as the percentage of all rodents known to be alive that are captured in a given trapping session. The enhanced trapping regime proposed for this study ensures that an even higher proportion of the mouse and chipmunk population on each plot is trapped regularly.

The standard trapping protocol for these plots is as follows. On day 1 at 16:00 h, all 242 traps on a plot are baited with crimped oats with sunflower seeds, when nighttime temperatures are expected to be below about 8° C. Traps are covered with a cover board for protection against rain and direct sun, and are provided with cotton nesting material in spring and fall. Between 07:30 h and about 10:30 h on day 2, all traps are checked. Empty traps are closed for the day. All captured animals are removed from the trap, provided with a uniquely numbered ear tag at first capture, and released at the point of capture following about 2 minutes of handling. During handling, the following data are recorded: ear tag number, sex, age (adult, subadult, juvenile, based on pelage), reproductive condition (for females, vulva perforate or not, pregnant or not, lactating or not; for males, testes abdominal or scrotal), body mass, numbers of ectoparasites (including ticks and botflies), and trap station. All traps are then reset beginning at 16:00 h. Traps are checked for a second time on day 3 and are then closed until the next trapping session begins 3-4 weeks later. The enhanced trapping regime includes the following changes: (1) traps are set for three (versus two) consecutive nights; (2) trapping is conducted every two (versus 3-4) weeks; (3) trapped rodents are outfitted with Passive Integrated Transponder (PIT) tags (versus eartags); and (4) small (1-mm diameter) ear punches are taken to assess each rodent's *B. burgdorferi*-infection status via PCR.

On the four control plots, traps are provided with crimped oat/sunflower seed bait. On all five experimental plots, this standard bait is replaced with bait containing freeze-dried vaccine. Consumption of part or all of the bait is noted. After rodents are released from handling, all unconsumed bait is placed in heavy gauge plastic bags and disposed of off site. The use of cover boards over the sheet metal traps ensures that the structural integrity of the bait is protected even on rainy nights. Bait is mixed with rhodamine B to assess bait intake, by checking mouse hair samples by fluorescence microscopy throughout the period of study. High capture probabilities ensure that very high proportions of the actual mouse and chipmunk populations gain access to the vaccine bait.

Ear punch samples from each mouse are frozen immediately and stored at −70° C. prior to being subjected to PCR, for detection of *B. burgdorferi*. Each animal captured in each trapping session is categorized as infected or uninfected based on the PCR analysis. Because of high capture probabilities, it is anticipated that individual mice and chipmunks are repeatedly captured in successive trapping sessions. Repeated analysis permits the time at which infection status changes from uninfected-to-infected to be determined. The hypothesis that the bait vaccine protects mice from *B. burgdorferi* infection is tested using repeated-measures ANOVA, with infection prevalence in the mouse population (angular transformed) as the dependent variable, and year and treatment as the main effects.

A significant treatment effect is expected, interpreted as a demonstration that the vaccine bait disrupts the transmission of *B. burgdorferi* from tick vector-to-reservoir host (disruption of the enzootic cycle of Lyme disease). The first year is anticipated to consist of vaccinating rodents that have already been exposed to *B. burgdorferi*. Consequently, a reduction in infection prevalence in rodents is not expected until after vaccination of hosts has caused a reduction in the transmission rate from ticks to hosts (via a reduction in the infection prevalence of nymphs). Nonetheless, an understanding of the mechanism(s) is not necessary in order to make and use the invention.

Questing nymphal ticks (those that have taken only one blood meal the previous year) are collected via standard drag sampling (Ostfeld et al., J Med Entomol, 33:90-95, 1996; and Ostfeld et al., Vector Borne Zoonotic Dis, 1:55-63, 2001) during the annual peak in host-seeking activity, which typically occurs in mid June to early July. The infection prevalence (percentage of nymphs infected with *B. burgdorferi*) is determined for several consecutive years on all of the plots. Such a long-term study is useful for assessing interannual variation in responses by both mice and ticks. White-footed mice at the IES site can vary more than an order of magnitude from one year to the next, and nymphal densities can vary more than 5-fold among years. To assess the potential effectiveness of the oral bait vaccine in natural settings, it is important to incorporate the impact of strongly varying natural populations of ticks and their hosts. A minimum of 200 nymphs from each plot are frozen immediately after collection and tested by PCR for the presence of *B. burgdorferi* nucleic acid (Guttman et al., J Clin Microbiol, 34:652-656, 1996; and Wang et al., Genetics, 151:15-30, 1999), as described in Example 12. This PCR protocol is specific for *B. burgdorferi* sensu stricto and is very sensitive, with results comparable to previous methods using immunofluorescence.

The reservoir competence or bacterial load of select New York wildlife was tested using semi-nested PCR with primers against OspC. Multiple species were examined including mice, chipmunks, deer, raccoons, opossums, skunks, shrews, birds, and squirrels. White-footed mice and chipmunks had the highest load of *B. burgdorferi*, 92% and 55% reservoir competence respectively (LoGiudice et al., Proc Natl Acad Sci USA, 100:567-571, 2003).

Questing nymphs feed only once during the larval stage, and represent the prevalence of *B. burgdorferi* in the area, as well as the risk of human exposure to Lyme disease. The infection prevalence in questing nymphs collected in experimental plots from 1-5 years after vaccine administration is compared to that found prior to vaccine administration, as well as to the nymphal infection prevalence on the control plots. Natural variance in infection prevalence is inferred from the long-term data collected on the control plots, as well as from data collected over the study period. Statistical comparisons are made between plots and time points, by repeated measures ANOVA, with year and treatment as the main effects. As for infection prevalence in hosts, a significant effect of treatment (with nymphal infection prevalence reduced on vaccinated grids), a significant effect of year (with later years having reduced infection prevalence), and a significant treatment by year interaction is expected. A significant reduction in nymphal infection prevalence on experimental plots is legitimately interpreted as representing a decreased risk of human exposure to Lyme borreliosis (LoGiudice et al., Proc Natl Acad Sci USA, 100:567-571, 2003). Nonetheless, an understanding of the mechanism(s) is not necessary in order to make and use the invention.

VII. Oral Vaccination of Human Subjects

Candidate lyophilized bacterial Lyme disease vaccines that have been shown to be safe and effective in laboratory mice, are tested in human volunteers in multicenter, randomized controlled clinical trials as known in the art (Sigal et al., N Engl J Med, 339:216-222, 1998; and Steere et al., N Engl J Med, 339:209-215, 1998). In particular, some preferred embodiments of the present invention are tested in healthy sero-negative human subjects aged 15 to 65 years old residing in areas of the United States where Lyme disease is endemic. Briefly, subjects are randomly assigned to an experimental group (e.g., *Lactobacillus plantarum* strain expressing the hLFA1-mutated OspA lipoprotein, Lp-OspAhLFA$^-$) or a placebo group (e.g., *Lactobacillus plantarum* transfected with an empty vector, Lp). The oral vaccines are administered to the subjects at study entry, one month later, three months later, and one year later. The subjects are followed for two years and are monitored for development of *B. burgdorferi* infection and Lyme disease by western blot and clinical examination). Preferred vaccines are contemplated to elicit a potent anti-Borrelia antibody response at six months post entry. Furthermore, preferred vaccines are contemplated to have a vaccine efficacy at one-year post entry of at least 50%, preferably at least 75%, more preferably at least 90% and most preferably at least 95%. Vaccine efficacy is calculated by dividing the number of experimental subjects that develop Lyme disease by the number of placebo subjects that develop Lyme disease.

The present invention further provides oral vaccine compositions comprising a generally recognized as safe bacterium engineered to express a *B. burgdorferi* outer surface protein, in combination with at least one other agent. In some embodiments, the at least one other agent is a biocompatible carrier including, but not limited to, saline, buffered saline, and water. In other embodiments, the at least one other agent is a food carrier or an excipient that enables the vaccine compositions to be formulated as tablets, pills, capsules, liquids, gels, syrups, slurries, suspensions and the like, for oral ingestion by a subject. Additionally, the vaccine compositions of the present invention are suitable for use with typical probiotic or symbiotic additives, as known in the art. The vaccine compositions of the present invention may be manufactured in a manner that is itself known (e.g., by means of conventional mixing, dissolving, granulating, dragee-making, levigating, emulsifying, encapsulating, entrapping or lyophilizing processes). Suitable excipients include but are not limited to carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage). Moreover, some oral vaccine compositions of the present invention comprise a suitable enteric-coating, and may be administered with an antacid.

VIII. Antigens of Other Pathogenic Bacteria

The recombinant nonpathogenic bacterial vaccine vectors and immunization methods of the present invention are also contemplated to find use in protecting mammals (including humans) from other disease-causing infectious agents, and in particular from other arthropod-borne bacteria. In the first place, some embodiments of the present invention comprise recombinant *E. coli* or *L. plantarum* expressing *Yersinia pestis* F1 capsule antigen (Caf1 set forth as SEQ ID NO:18) or low calcium response locus protein V (LvrV set forth as SEQ ID NO:19), for use as a Plague vaccine. Additional vaccines of the present invention comprise recombinant *E. coli* or *L. plantarum* expressing a *Rickettsia rickettsii* surface antigen (e.g., OmpA or OmpB), for use as a Rocky Mountain spotted fever vaccine.

Other vaccines of the present invention comprise *E. coli* or *L. plantarum* engineered to express one or more pathogenic bacterial antigens. In some embodiments, the pathogenic bacterial antigens are selected from but not limited to: protective antigen (Pa) of *Bacillus anthracis* (e.g., anthrax vaccine); low molecular weight outer-membrane protein (OMP) of *Escherichia coli* O157:H7 (e.g., diarrhea vaccine); urease subunit B (UreB) of *Helicobacter pylori* (e.g., ulcer vaccine); outer membrane protein-macromolecular complex (OMP-MC) of *Neisseria gonorrhoeae* (e.g., gonorrhea vaccine); outer membrane protein F (OmpF) *Pseudomonas aeruginosa* (e.g., nosocomial infection vaccine); and pneumococcal surface adhesin A (PsaA) or pneumococcal surface protein A (PspA) of *Streptococcus pneumoniae* (e.g., pneumonia vaccine). In still further embodiments, the present invention provides: pneumonia/meningitis vaccines comprising antigen(s) from *Haemophilus influenzae* type b; otitis/sinusitis/lower respiratory tract vaccines comprising antigen(s) *Moraxella catarrhalis*; food poisoning vaccines comprising antigen(s) from *Salmonella enterica* or *Salmonella enteritides*; and cholera vaccines comprising antigen(s) from *Vibrio cholera*. In some embodiments, fragments of the antigen(s) of interest retain their own leader sequence or lack a leader sequence entirely.

EXAMPLES

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); U (units), mU (milliunits); min. (minutes); sec. (seconds); % (percent); kb (kilobase); bp (base pair); PCR (polymerase chain reaction); Osp (outer surface protein); Ec. (*E. coli*); Lp (*L. plantarum*); WT (wild type); Th (helper T cell); MHC (major histocompatibility complex); TNF (tumor necorsis factor); IFNγ (interferon-gamma); mAb (monoclonal antibody), mIg (membrane immunoglobulin); APC (antigen presenting cell); MO (macrophage); LN (lymph node); SN (supernatant); RS (restriction site); ELISA (enzyme linked immunosorbent assay); 1° (primary); 2° (secondary); IPTG (isopropyl B-D-thiogalactopyranoside); and OD (optical density).

Example 1

Lyophilization of Recombinant Bacteria Expressing *B. burgdorferi* Antigens

*Escherichia coli* BL21 (DE3) pLysS carrying a plasmid of interest (pET9c-OspA, pET9c-C1, pET9c-C12, pET9c-C1.C12 or pET9c-OspCx.A) is induced for protein expression with IPTG when the $OD_{600}$ reaches 0.4. Bacterial cells are grown for 3 hr and harvested at 5000 g for 10 min at 4° C. Cells are re-suspended in 20 ml of TBY containing 24% sucrose (Gu et al., J Biotechnol, 88:95-105, 2001). Ten ml of cells are transferred to a 50 ml glass tube and are quickly frozen in a bath of dry-ice/ethanol. The tubes are tilted while freezing to get a greater surface area. These tubes are placed in lyophilizer overnight for 24 hr after which the tubes are placed −70° C. for storage until use. This method is also contemplated to be suitable for freeze drying *Lactobacillus* spp.

Example 2

Purification of Recombinant *B. burgdorferi* Proteins

*Escherichia coli* (strain BL21(DE3)pLysS) transformed with the pET9c plasmid encoding one or more *B. burgdorferi* gene(s) is grown in 1000 ml LB media (5 µl NaCl, 10 µl tryptone, 5 g/l yeast extract, 25 µg/l chloramphenicol and 30 µg/l kanamycin) at 37° C., with shaking. When the $OD_{600}$ of the cultures reaches 0.4-0.6, protein expression is induced by the addition of IPTG to a final concentration of 0.5 mM, and cells are then grown for another 4 hr. The cultures are harvested by centrifugation at 3800 g for 5 min, and the cells are resuspended in 30 ml of 20 mM NaPO4, pH 7.7. The crude extracts are stored at −20° C. overnight. The frozen cell suspensions are incubated at 4° C. for 12-14 h in the presence of a protease inhibitor cocktail solution (Roche). Once thawed, the cell suspensions are incubated at room temperature with DNase I (6.7 µg/ml) and 5 mM of $MgCl_2$ for 30 min. Cellular debris is pelleted by centrifugation at 15000×g for 20 minutes at 4° C., leaving a "crude extract" (supernatant). Recombinant protein is further purified as follows: 1) the crude extract is applied directly to a chromatography column containing 75 ml Q-Sepharose Fast Flow (Pharmacia) equilibrated with 20 mM Tris-HCl pH 7.5; 2) the recombinant protein is eluted off the column with the same buffer (20 mM Tris-HCl pH 7.5) and 45 ml fractions are collected; 3) each fraction is analyzed by SDS-PAGE to identify where the recombinant protein is eluted; 4) the fractions containing the most recombinant protein are combined and concentrated to approximately 7 ml with a 10-50 Kd centriprep concentrator (Amicon). The protein concentration is measured by the Bradford method using the BioRad protein assay and the protein is stored at −70° C. The purity and reactivity of the recombinant proteins is then assessed by SDS-PAGE and western blot.

Example 3

Enzyme Linked Immunosorbent Assay (ELISA)

Purified *B. burgdorferi* protein is used to coat ELISA plastic microwell plates (MAXISORP™, Nunc) at a concentration of 2.5 µg/ml in coating buffer (100 mM Bis-Tris Propane pH 9.7 containing 0.02% sodium azide) at 100 µl/well. The microwell plates are incubated at 37° C. for 1 hr. The solution is decanted from the wells and the plates are washed three times with 300 µl/well of TBST solution (26 mM Tris Base, 0.137 M NaCl, 0.01% Tween 20, 0.02% sodium azide). The microwell plates are blocked with 300 µl/well blocking buffer (100mM Bis-Tris Propane pH9.7, 3.0% dry milk, 0.1% Tween 20, 0.02% sodium azide). Following 1hr incubation at 37° C. the plates are washed three times. The antibody-binding procedure for the ELISA assay is as follows: serum samples are diluted 1:100 or 1:1000 in specimen diluent (20mM Tris Base pH 7.5, 136 mM sodium chloride, 1.0% dry milk, 0.10% Tween 20, 0.02% sodium azide) at 100 µl/well and incubated for 1 hr at 37° C. The solution is decanted from the wells and the plates washed three times with 300 µl/well TBST solution. The secondary antibody is a goat anti-mouse alkaline phosphatase conjugate (Jackson Immunoresearch Laboratories) used at 0.6 mg/ml in specimen diluent at 100 µl/well. The plates are incubated at 37° C. for 1 hr and then washed three times. Development of the assay is performed using p-nitrophenylphosphate phosphatase substrate (Kirkegaard & Perry Laboratories) at 100 µl/well. Following a 30-minute incubation period at 37° C., the reaction is stopped with 5% EDTA at 100µl/well and the plate read at an absorbance of 405nm on a microplate reader.

Example 4

OspA and OspC Western Blot

Five monoclonal antibodies (mAb) are used as primary antibodies to characterize *B. burgdorferi* OspA and OspC proteins by western blot: mab 184.1, 105.5, 336.1 and LA2.2 are used to check OspA; and mAb3.8 is used to check several OspC groups since it binds to the most C-terminal region of OspC (an epitope that is conserved in all 22 OspC groups). The mAb 184.1 binds to a region of OspA centered around residue 61 (Schubach et al., Infect Immun, 59:1911-1915, 1991). The mAb 105.5 binds to an epitope of OspA centered around residue 214, and is able to agglutinate *B. burgdorferi* B31 in vitro (Schubach et al., supra, 1991). The mAb 336.1 was raised against *B. afzelii* strain Pgau, and binds to the C-terminal alpha-helix of OspA strain B31 (McGrath et al., Infect Immun, 63:1356-1361, 1995). The mAb LA2.2 defines an important protective B cell epitope of OspA (Schaible et al., Proc Natl Acad Sci USA, 87:3768-3772, 1990; and Simon et al., J Infect Dis, 164:123-132, 1991), between amino acids 143-273 (Wilske et al., Med Microbiol Immunol, 181:191-207, 1992). The mAb LA2 specifically recognizes the three surface exposed loops of the C-terminal domain of OspA that are on the tip of the elongated molecule most distant from the lipidated N-terminus (Ding et al., J Mol Biol, 302:1153-1164, 2000), and binds to strain B31 (*B. burgdorferi*) with some avidity. Low levels of anti-OspA Abs that are equivalent to mAb LA-2, are associated with incomplete protection from *B. burgdorferi* infection of hamsters vaccinated with unlipidated OspA (Johnson et al., Vaccine, 13:1086-1094, 1995). The secondary antibody used in the western blot analysis is an alkaline phosphatase labeled anti-mouse IgG.

In an exemplary study, *E. coli* BL21(DE3)pLysS expressing *B. burgdorferi* OspA (Ec-A) was freeze-dried and a suspension (15 μl) of this induced culture (about $10^7$ cells) was run on a 10-20% Tris-HCl, SDS-PAGE gel to verify expression of recombinant OspA. OspA lipoprotein concentration was determined by Coomassie staining of the gel to be about 0.1 mg/ml. Protein expression was confirmed by western blot using the anti-OspA mAb LA2.2 (See, FIG. 1).

In another exemplary study, *B. burgdorferi* genes, ospA and a chimera of ospC1 and ospA, have been cloned and expressed in *Lactobacillus plantarum* strain 256 (Lp-A and Lp-C1.A, respectively). Protein expression was confirmed by western blot using a combination of anti-OspC and OspA mAbs (See, FIG. 2).

Example 5

Oral Gavage Inoculation of Lyophilized Bacterial Lyme Disease Vaccine

Vaccine efficacy is tested in a Lyme disease susceptible strain of inbred mice, C3H/HeJ (Jackson Laboratory). A protocol adapted from published reports is used (Fikrig et al., J Infect Dis, 164:1224-1227, 1991; and Luke et al., Vaccine, 15:739-746, 1997). Freeze-dried IPTG-induced bacteria are weighed and suspended in TBY to an $OD_{600}=1$ (approximately $10^9$ cells/ml) and 250 μl ($2.5\times10^8$ *E. coli* cells) are inoculated by oral gavage with a ball tipped disposable feeding needle, 20 gauge, 1.5 inch (Popper and Son Inc., NY). Mice are anesthetized with isofluorane before inoculation.

Approximately 6-8 wk old mice receive the first immunization daily for 5 days (days 1, 2, 3, 4, 5). Three days later, the 1st round of boosts is performed (days 8, 9, 10, 11, 12). Two weeks after the last boost, mice are bled (day 27) by approved protocol. The sera are tested with an ELISA for the presence of IgG to the immunogen (systemic immunity). If antibody titers are below OD 0.5 against purified OspA, then mice are boosted again for 5 additional consecutive days, and challenged two weeks later.

Example 6

Intradermal B. burgdorferi Challenge

Two days after measuring antibody titer (day 30), orally immunized mice are challenged with *B. burgdorferi* by intradermal (ID) inoculation of $2\times10^3$ *B. burgdorferi* B31 (or by infected tick inoculation). Two weeks later (day 45) mice are terminated and blood and tissues are obtained to assess protection and/or disease. Vaccine protection is tested by culture of the aseptically harvested heart in BSK media without antibiotic, followed by confirmation with nested PCR of the same culture. Vaccine protection is also tested by PCR of the ear tissue to assess bacterial dissemination, as well as by neutralization assays, western blot and measurement of LA2 equivalent antibodies in serum.

Example 7

Production of B. burgdorferi-Infected Ixodes Ticks

Approximately $2-5\times10^3$ spirochetes of low passage *B. burgdorferi* senso stricto in 100 µl of BSK with serum are inoculated intradermally into two or three C3H-HeJ mice. Three weeks later the mice are bled, serum collected and tested by ELISA against whole cell sonicated B31 spirochetes to confirm infection.

The tick colony used during development of the present invention was obtained from *Ixodes* scapularis ticks collected at Shelter Island, N.Y. during the fall of 2001. Several pairs of adult males and females are placed on the ears of a New Zealand white rabbit and allowed to feed to repletion for 5 days. The females are then placed individually into 50 ml Falcon tubes with saturated humidity and allowed to lay eggs. Larvae begin emerging 45 days later. About one month after hatching, during which all ticks hatch and their cuticles harden, batches of larvae (about 100) are placed around the dorsal neck and head region of restrained C3H-HeJ mice and allowed to feed to repletion. Three days later, replete larva begin to fall off the mice and are collected into 50 ml Falcon tubes. These tubes are kept at room temperature with saturated humidity. Replete ticks are placed in 50 ml Falcon tubes and allowed to molt to the nymphal stage. Several ticks are tested for infection by crushing followed by darkfield microscopy and/or by PCR. This procedure generally results in about 90% tick infection rate.

Example 8

Challenge with B. burgdorferi-Infected Ticks

A Biohazard room is secured with tape around all possible points of exit (door and air ducts) and coated with a barrier (¼ inch) of sticky substance (Tree Tanglefoot) to prevent possible tick escape. Mice are placed individually into specially constructed hardware cloth cages (0.25-inch mesh), which in turn are placed within a plastic pan containing water. These cages have been approved for use by mice, by a veterinarian. The cages are constructed as to not require bedding, and are situated to rest on a base approximately one half inch above the water level. The upper edge of each pan contains one 0.25 inch smear of Tanglefoot (The Tanglefoot Company, Grand Rapids, Mich.) above the water line to prevent tick escape. Engorged ticks drop readily through the mesh into the pan. Field ticks are checked for infection by PCR as described in Example 12. The rate of infection obtained for eastern Long Island ticks is about 20-30%. Between 8-10 infected (field or laboratory infected) nymphal ticks are placed on each individual via the use of fine tipped forceps. The number of ticks placed on each mouse is dictated by the percentage of ticks that are infected with *B. burgdorferi*, as determined by darkfield microscopy of tritiated ticks. A minimum of half the ticks placed on each animal must be infected to insure a successful challenge. The ticks feed on each animal 4-5 days and then drop naturally from the host. Mice are kept in the special cages for an additional day to insure tick feeding is completed and that no ticks are able to escape to the contained environment.

Example 9

Determination of B. burgdorferi Infection by Western Blot

The MarDx *B. burgdorferi* western blot (MarDx Diagnostics, Inc, Carlsbad, Calif.) is used to check protection of mice that have been vaccinated and challenged (by needle or by tick inoculation), according to the manufacturer's instructions. Mice are scored as infected when five out of ten bands are positive on the IgG western blot (93 Kd, 66 Kd, 58 Kd, 45 Kd, 41 Kd, 39 Kd, 30 Kd, 28 Kd, 23 Kd, 18 Kd). Since the vaccine tested contains OspA and/or OspC, and antibodies to these antigen(s) prevent infection from taking place, the presence of antibodies to all other *Borrelia* antigens (other than OspA at 30 Kd and/or OspC at 22 Kd) is indicative of *B. burgdorferi* infection.

Example 10

B. burgdorferi Neutralization Assay

To assess the immunogenicity of the oral Lyme disease vaccine, neutralization assays are carried out with sera from vaccinated mice, and several different strains of *B. burgdorferi*. In vitro growth inhibitory activity of mouse sera is assessed as previously described (Johnston et al., Vaccine, 13:1086-1094, 1995; Sadziene et al., J Infect Dis, 167:165-172, 1993; and Luke et al., Vaccine, 15:739-746, 1997). Briefly, growth inhibition titers are determined in flat-bottomed microtiter plates. The initial inoculum of spirochetes (*B. burgdorferi*, B31, high passage) is $2\times10^6$ in 100 µl. Mouse sera is diluted 1:8 in fresh BSK II medium, filtered (0.2 µm) and heat inactivated (56° C., 30 min). Filter sterilized guinea pig complement (Gibco) is added to each well to a final concentration of 19 hemolytic units per ml of medium, after addition of antibody. Plates are incubated in a humidified environment in a sealed dessicator at 33° C. for 72 hr. Wells are monitored visually for changes in color of the Phenol Red indicator, and by dark field microscopy of suspended cultures. Bacterial lysis, immobilization and/or agglutination are scored after microscopic evaluation. The IgG fraction of a hyperimmune rabbit serum, raised against *B. burgdorferi* (growth inhibition titer of 1:20, 480) is used as a positive control. The growth inhibitory titer is defined as the highest dilution of antiserum that results in pink (rather than yellow) wells, representing at least 20-fold fewer cells than in wells without immune serum.

Example 11

LA2 Equivalent Assay

An association between serum LA2 equivalent titer, as measured by the ability of serum to inhibit *B. burgdorferi* in vitro, and protection of hamsters from infection has previously been reported (Johnson et al., Vaccine, 13:1086-1094, 1995). Since high LA2 equivalent titer has been related to vaccine efficacy and protection from infection, the LA2 equivalent titers of sera from orally vaccinated mice are measured with a mAb LA2 competition ELISA. Briefly, ELISA plates are coated with OspA purified as described in Example 2. Wells are blocked with 1% polyvinyl alcohol (PVA), for 1 hr at 37° C. Plates are washed once we PBS/Tween, then twice with PBS. All antibodies are diluted in PVA/PBS/Tween, containing 0.1% non-immune mouse sera, and tested in triplicate. Five serial two-fold dilutions of LA2 mAb are used to establish the reference curve beginning at 500 ng/ml. Plates are incubated for 1 hr at 37° C. and washed. Biotinylated LA2 (100 µl, 380 ng/ml) is added to all wells, incubated for 1 hr at 37° C. and then washed. Peroxidase-labeled streptavidin (KPL) is diluted in PVA/PBS/Tween20 and added to all wells. Following a final 1 hr incubation period at 37° C., plates are washed. Peroxidase substrate is added and the $OD_{450}$ is measured. A reference curve is obtained from non-conjugated LA2 values using exponential regression analysis. LA2 µg equivalent for the mouse polyclonal sera is determined by interpolation from the reference curve.

Example 12

PCR Detection of *B. burgdorferi*

This example provides PCR methods for detecting whether mouse hosts and tick vectors are infected with *B. burgdorferi*. Briefly, ear and heart tissue from challenged mice is weighed, and to 5-80 mg of tissue is added 200 µl of a 1 mg/ml Collagenase A solution. Followed by a 4 hr incubation period at 37° C., 0.200 µl of a 1 mg/ml Proteinase K solution is added in digestion buffer (200 mM NaCl, 20 mM TrisCl pH 8, 50 mM EDTA, 1% SDS), and incubated overnight at 50-55° C. The following day the samples are spun at maximum speed, boiled for 30 min in screw cap tubes, and spun again for 15 min at maximum speed. DNA is obtained by phenol-chloroform-isoamyl alcohol extraction of the resulting supernatant. DNA is precipitated from the supernatant with ethanol, and resuspended in 25 µl of water. The DNA is then purified with Chelex as follows: 475 µl of 5% chelex is added to 25 µl of DNA, vortexed for 30 seq and incubated overnight at 56° C. The next day, the samples are vortexed for 30 sec incubated at 95° C. for 15 minutes, vortexed again for 30 sec and spun down for 5 min at maximum speed. The supernatant is removed to a fresh tube and 10 µl is used in a 50 µl real time PCR reaction as known in the art (Wang et al., J Infect Dis, 186:782-791, 2002).

Briefly, to detect *B. burgdorferi* DNA in infected ticks, a single tick is smashed against the walls of an eppendorf tube with a pipet tip, and suspended in 25 Ill of water. To this solution, 475 µl of 5% Chelex is added, vortexed for 30 sec, and incubated overnight at 56° C. The next day, the samples are vortexed for 30 seq incubated at 95° C. for 15 minutes (or boiled), vortexed a second time for 30 sec, and spun down for 5 min at maximum speed in a microfuge. The supernatant is removed to a fresh tube and 10 µl is used in a 50 µl PCR reaction, as described (Guttman et al., J Clin Microbiol, 34:652-656, 1996; and Wang et al., Genetics, 151:15-30, 1999).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in microbiology, molecular biology, genetics, or related fields, are intended to be within the scope of the following claims.

We claim:

1. A method of immunizing a subject comprising:
   a) providing an oral vaccine composition comprising a lyophilized *Escherichia coli*, and *Lactobacillus plantarum* bacterium engineered to express a protein comprising a modified amino acid sequence set forth herein as SEQ ID NO:2, wherein said modified SEQ ID NO:2 comprises a deletion of hLFA1 epitope SEQ ID NO:5 (YVLEGTLTA), and
   b) orally administering said oral vaccine composition to a subject under conditions suitable for eliciting an antibody response in said subject against a *Borrelia burgdorferi* outer surface protein.

2. The method of claim 1, wherein said oral vaccine composition further comprises a food carrier or an excipient.

3. The method of claim 1, wherein said subject is a mammal.

4. The method of claim 3, wherein said mammal is a feral animal comprising one or more of a mouse, a chipmunk, a squirrel, a shrew, a vole, a rat, a raccoon, an opossum, a skunk, a rabbit, and a deer.

5. The method of claim 3, wherein said mammal is a domesticated animal comprising one or more of a dog, a cat, a cow, and a horse.

6. The method of claim 1, wherein said antibody response comprises an outer surface protein-reactive serum IgG titer of at least 1:100.

7. The method of claim 1, wherein said orally administering comprises more than one meal.

8. The method of claim 1, wherein said bacterium comprises a *lactobacillus* selected from the group consisting of *L. acidophilus, L. brevis, L. casei, L. crispatus, L. fermentum, L. gasseri, L. plantarum, L. reuteri, L. rhamnosus*, and *L. salivarius*.

9. The method of claim 2, wherein said food carrier comprises a dairy product selected from the group consisting of milk, yogurt, and cheese, or a grain product selected from the group consisting of grain, seed, bread, and cereal.

10. The method of claim 2, wherein said excipient is selected from the group consisting of a sugar, a starch, a gum, and a protein.

11. The method of claim 2, wherein said food carrier comprises animal chow.

* * * * *

SEQUENCE LISTING

```
<160> NUMBER OF SEQ ID NOS: 19

<210> SEQ ID NO 1
<211> LENGTH: 822
<212> TYPE: DNA
<213> ORGANISM: Borrelia burgdorferi

<400> SEQUENCE: 1
atgaaaaaat atttattggg aataggtcta atattagcct taatagcatg taagcaaaat      60
gttagcagcc ttgacgagaa aaacagcgtt tcagtagatt tgcctggtga aatgaaagtt     120
cttgtaagca aagaaaaaaa caaagacggc aagtacgatc taattgcaac agtagacaag     180
cttgagctta aaggaacttc tgataaaaac aatggatctg gagtacttga aggcgtaaaa     240
gctgacaaaa gtaaagtaaa attaacaatt tctgacgatc taggtcaaac cacacttgaa     300
gttttcaaag aagatggcaa aacactagta tcaaaaaaag taacttccaa agacaagtca     360
tcaacagaag aaaaattcaa tgaaaaaggt gaagtatctg aaaaaataat aacaagagca     420
gacggaacca gacttgaata cacaggaatt aaaagcgatg gatctggaaa agctaaagag     480
gttttaaaag gctatgttct tgaaggaact ctaactgctg aaaaaacaac attggtggtt     540
aaagaaggaa ctgttacttt aagcaaaaat atttcaaaat ctgggggaagt ttcagttgaa     600 cttaatgaca ctgacagtag tgctgctact aaaaaaactg cagcttggaa ttcaggcact     660
tcaactttaa caattactgt aaacagtaaa aaaactaaag accttgtgtt tacaaaagaa     720
```

```
aacacaatta cagtacaaca atacgactca aatggcacca aattagaggg gtcagcagtt    780
gaaattacaa aacttgatga aattaaaaac gctttaaaat aa                       822
```

<210> SEQ ID NO 2
<211> LENGTH: 273
<212> TYPE: PRT
<213> ORGANISM: Borrelia burgdorferi

<400> SEQUENCE: 2

```
Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn

```
gaggttgaag cgttgctgtc atctatagat gaaattgctg ctaaagctat tggtaaaaaa    240
atacaccaaa ataatggttt ggataccgaa aataatcaca atggatcatt gttagcggga    300
gcttatgcaa tatcaaccct aataaaacaa aaattagatg gattgaaaaa tgaaggatta    360
aaggaaaaaa ttgatgcggc taagaaatgt tctgaaacat ttactaataa attaaaagaa    420
aaacacacag atcttggtaa agaaggtgtt actgatgctg atgcaaaaga agccatttta    480
aaagcaaatg gtactaaaac taaggtgct gaagaacttg gaaaattatt tgaatcagta    540
gaggtcttgt caaaagcagc taagagatg cttgctaatt cagttaaaga gcttacaagc    600
cctgttgtgg cagaaagtcc aaaaaaacct taa                                 633
```

<210> SEQ ID NO 4
<211> LENGTH: 210
<212> TYPE: PRT
<213> ORGANISM: Borrelia burgdorferi

<400> SEQUENCE: 4

```
Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Asn Lys Lys
        35                  40                  45

Ile Thr Asp Ser Asn Ala Val Leu Leu Ala Val Lys Glu Val Glu Ala
    50                  55                  60

Leu Leu Ser Ser Ile Asp Glu Ile Ala Ala Ala Ile Gly Lys Lys
65                  70                  75                  80

Ile His Gln Asn Asn Gly Leu Asp Thr Glu Asn Asn His Asn Gly Ser
                85                  90                  95

Leu Leu Ala Gly Ala Tyr Ala Ile Ser Thr Leu Ile Lys Gln Lys Leu
            100                 105                 110

Asp Gly Leu Lys Asn Glu Gly Leu Lys Glu Lys Ile Asp Ala Ala Lys
        115                 120                 125

Lys Cys Ser Glu Thr Phe Thr Asn Lys Leu Lys Glu Lys His Thr Asp
    130                 135                 140

Leu Gly Lys Glu Gly Val Thr Asp Ala Asp Ala Lys Glu Ala Ile Leu
145                 150                 155                 160

Lys Ala Asn Gly Thr Lys Thr Lys Gly Ala Glu Glu Leu Gly Lys Leu
                165                 170                 175

Phe Glu Ser Val Glu Val Leu Ser Lys Ala Ala Lys Glu Met Leu Ala
            180                 185                 190

Asn Ser Val Lys Glu Leu Thr Ser Pro Val Val Ala Glu Ser Pro Lys
        195                 200                 205

Lys Pro
    210
```

<210> SEQ ID NO 5
<211> LENGTH: 9
<212> TYPE: PRT
<213> ORGANISM: Borrelia burgdorferi

<400> SEQUENCE: 5

```
Tyr Val Leu Glu Gly Thr Leu Thr Ala
1               5
```

```
<210> SEQ ID NO 6
<211> LENGTH: 211
<212> TYPE: PRT
<213> ORGANISM: Borrelia burgdorferi

<400> SEQUENCE: 6

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Ser Lys Lys
        35                  40                  45

Ile Thr Glu Ser Asn Ala Val Val Leu Ala Val Lys Glu Ile Glu Thr
    50                  55                  60

Leu Leu Ala Ser Ile Asp Glu Leu Ala Thr Lys Ala Ile Gly Lys Lys
65                  70                  75                  80

Ile Gln Gln Asn Gly Gly Leu Ala Val Glu Ala Gly His Asn Gly Thr
                85                  90                  95

Leu Leu Ala Gly Ala Tyr Thr Ile Ser Lys Leu Ile Thr Gln Lys Leu
            100                 105                 110

Asp Gly Leu Lys Asn Ser Glu Lys Leu Lys Glu Lys Ile Glu Asn Ala
        115                 120                 125

Lys Lys Cys Ser Glu Asp Phe Thr Lys Lys Leu Glu Gly Glu His Ala
    130                 135                 140

Gln Leu Gly Ile Glu Asn Val Thr Asp Glu Asn Ala Lys Lys Ala Ile
145                 150                 155                 160

Leu Ile Thr Asp Ala Ala Lys Asp Lys Gly Ala Ala Glu Leu Glu Lys
                165                 170                 175

Leu Phe Lys Ala Val Glu Asn Leu Ala Lys Ala Ala Lys Glu Met Leu
            180                 185                 190

Ala Asn Ser Val Lys Glu Leu Thr Ser Pro Ile Val Ala Glu Ser Pro
        195                 200                 205

Lys Lys Pro
    210

<210> SEQ ID NO 7
<211> LENGTH: 273
<212> TYPE: PRT
<213> ORGANISM: Borrelia burgdorferi

<400> SEQUENCE: 7

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
```

```
            115                 120                 125
Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Phe Thr Leu Glu Gly Lys Val Ala Asn Asp Lys Val
                165                 170                 175

Thr Leu Glu Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Lys Thr Ser Thr Leu Thr
    210                 215                 220

Ile Ser Val Asn Ser Lys Lys Thr Thr Gln Leu Val Phe Thr Lys Gln
225                 230                 235                 240

Asp Thr Ile Thr Val Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Lys

<210> SEQ ID NO 8
<211> LENGTH: 469
<212> TYPE: PRT
<213> ORGANISM: Borrelia burgdorferi

<400> SEQUENCE: 8

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Asn Lys Lys
        35                  40                  45

Ile Thr Asp Ser Asn Ala Val Leu Leu Ala Val Lys Glu Val Glu Ala
    50                  55                  60

Leu Leu Ser Ser Ile Asp Glu Ile Ala Ala Lys Ala Ile Gly Lys Lys
65                  70                  75                  80

Ile His Gln Asn Asn Gly Leu Asp Thr Glu Asn Asn His Asn Gly Ser
                85                  90                  95

Leu Leu Ala Gly Ala Tyr Ala Ile Ser Thr Leu Ile Lys Gln Lys Leu
            100                 105                 110

Asp Gly Leu Lys Asn Glu Gly Leu Lys Glu Lys Ile Asp Ala Ala Lys
        115                 120                 125

Lys Cys Ser Glu Thr Phe Thr Asn Lys Leu Lys Glu Lys His Thr Asp
    130                 135                 140

Leu Gly Lys Glu Gly Val Thr Asp Ala Asp Ala Lys Glu Ala Ile Leu
145                 150                 155                 160

Lys Ala Asn Gly Thr Lys Thr Lys Gly Ala Glu Glu Leu Gly Lys Leu
                165                 170                 175

Phe Glu Ser Val Glu Val Leu Ser Lys Ala Ala Lys Glu Met Leu Ala
            180                 185                 190

Asn Ser Val Lys Glu Leu Thr Ser Pro Val Val Ala Glu Ser Pro Lys
        195                 200                 205

Lys Pro Ser Met Ala Lys Gln Asn Val Ser Ser Leu Asp Glu Lys Asn
```

```
            210                 215                 220
Ser Val Ser Val Asp Leu Pro Gly Glu Met Lys Val Leu Val Ser Lys
225                 230                 235                 240

Glu Lys Asn Lys Asp Gly Lys Tyr Asp Leu Ile Ala Thr Val Asp Lys
                245                 250                 255

Leu Glu Leu Lys Gly Thr Ser Asp Lys Asn Asn Gly Ser Gly Val Leu
                260                 265                 270

Glu Gly Val Lys Ala Asp Lys Ser Lys Val Lys Leu Thr Ile Ser Asp
                275                 280                 285

Asp Leu Gly Gln Thr Thr Leu Glu Val Phe Lys Glu Asp Gly Lys Thr
290                 295                 300

Leu Val Ser Lys Lys Val Thr Ser Lys Asp Lys Ser Ser Thr Glu Glu
305                 310                 315                 320

Lys Phe Asn Glu Lys Gly Glu Val Ser Glu Lys Ile Ile Thr Arg Ala
                325                 330                 335

Asp Gly Thr Arg Leu Glu Tyr Thr Gly Ile Lys Ser Asp Gly Ser Gly
                340                 345                 350

Lys Ala Lys Glu Val Leu Lys Gly Tyr Val Leu Glu Gly Thr Leu Thr
                355                 360                 365

Ala Glu Lys Thr Thr Leu Val Val Lys Glu Gly Thr Val Thr Leu Ser
370                 375                 380

Lys Asn Ile Ser Lys Ser Gly Glu Val Ser Val Glu Leu Asn Asp Thr
385                 390                 395                 400

Asp Ser Ser Ala Ala Thr Lys Lys Thr Ala Ala Trp Asn Ser Gly Thr
                405                 410                 415

Ser Thr Leu Thr Ile Thr Val Asn Ser Lys Lys Thr Lys Asp Leu Val
                420                 425                 430

Phe Thr Lys Glu Asn Thr Ile Thr Val Gln Gln Tyr Asp Ser Asn Gly
                435                 440                 445

Thr Lys Leu Glu Gly Ser Ala Val Glu Ile Thr Lys Leu Asp Glu Ile
                450                 455                 460

Lys Asn Ala Leu Lys
465

<210> SEQ ID NO 9
<211> LENGTH: 456
<212> TYPE: PRT
<213> ORGANISM: Borrelia burgdorferi

<400> SEQUENCE: 9

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
                20                  25                  30

Ala Asp Glu Ser Val Lys Gly Pro Asn Leu Thr Glu Ile Asn Lys Lys
            35                  40                  45

Ile Thr Asp Ser Asn Ala Val Leu Leu Ala Val Lys Glu Val Glu Ala
        50                  55                  60

Leu Leu Ser Ser Ile Asp Glu Ile Ala Ala Lys Ala Ile Gly Lys Lys
65                  70                  75                  80

Ile His Gln Asn Asn Gly Leu Asp Thr Glu Asn Asn His Asn Gly Ser
                85                  90                  95

Leu Leu Ala Gly Ala Tyr Ala Ile Ser Thr Leu Ile Lys Gln Lys Leu
                100                 105                 110
```

```
Asp Gly Leu Lys Asn Glu Gly Leu Lys Glu Lys Ile Asp Ala Ala Lys
        115                 120                 125

Lys Cys Ser Glu Thr Phe Thr Asn Lys Leu Lys Glu Lys His Thr Asp
130                 135                 140

Leu Gly Lys Glu Gly Val Thr Asp Ala Asp Ala Lys Glu Ala Ile Leu
145                 150                 155                 160

Lys Ala Asn Gly Thr Lys Thr Lys Gly Ala Glu Leu Gly Lys Leu
            165                 170                 175

Phe Glu Ser Val Glu Val Leu Ser Lys Ala Ala Lys Glu Met Leu Ala
                180                 185                 190

Asn Ser Val Lys Glu Leu Thr Ser Pro Val Ala Glu Ser Pro Lys
            195                 200                 205

Lys Pro Ser Met Ala Val Ser Val Asp Leu Pro Gly Glu Met Lys Val
210                 215                 220

Leu Val Ser Lys Glu Lys Asn Lys Asp Gly Lys Tyr Asp Leu Ile Ala
225                 230                 235                 240

Thr Val Asp Lys Leu Glu Leu Lys Gly Thr Ser Asp Lys Asn Asn Gly
                245                 250                 255

Ser Gly Val Leu Glu Gly Val Lys Ala Asp Lys Ser Lys Val Lys Leu
            260                 265                 270

Thr Ile Ser Asp Asp Leu Gly Gln Thr Thr Leu Glu Val Phe Lys Glu
275                 280                 285

Asp Gly Lys Thr Leu Val Ser Lys Lys Val Thr Ser Lys Asp Lys Ser
        290                 295                 300

Ser Thr Glu Glu Lys Phe Asn Glu Lys Gly Glu Val Ser Glu Lys Ile
305                 310                 315                 320

Ile Thr Arg Ala Asp Gly Thr Arg Leu Glu Tyr Thr Gly Ile Lys Ser
                325                 330                 335

Asp Gly Ser Gly Lys Ala Lys Glu Val Leu Lys Gly Phe Thr Leu Glu
            340                 345                 350

Gly Lys Val Ala Asn Asp Lys Val Thr Leu Glu Val Lys Glu Gly Thr
        355                 360                 365

Val Thr Leu Ser Lys Ile Ser Lys Ser Gly Glu Val Ser Val Glu Leu
370                 375                 380

Asn Asp Thr Asp Ser Ser Ala Ala Thr Lys Lys Thr Ala Ala Trp Asn
385                 390                 395                 400

Ser Lys Thr Ser Thr Leu Thr Ile Ser Val Asn Ser Lys Lys Thr Thr
                405                 410                 415

Gln Leu Val Phe Thr Lys Gln Asp Thr Ile Thr Val Gln Lys Tyr Asp
            420                 425                 430

Ser Ala Gly Thr Asn Leu Glu Gly Thr Ala Val Glu Ile Lys Thr Leu
        435                 440                 445

Asp Glu Leu Lys Asn Ala Leu Lys
450                 455

<210> SEQ ID NO 10
<211> LENGTH: 453
<212> TYPE: PRT
<213> ORGANISM: Borrelia burgdorferi

<400> SEQUENCE: 10

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Asn Lys Lys
            20                  25                  30
```

```
Ile Thr Asp Ser Asn Ala Val Leu Leu Ala Val Lys Glu Val Glu Ala
        35                  40                  45
Leu Leu Ser Ser Ile Asp Glu Ile Ala Ala Lys Ala Ile Gly Lys Lys
50                  55                  60
Ile His Gln Asn Asn Gly Leu Asp Thr Glu Asn Asn His Asn Gly Ser
65                  70                  75                  80
Leu Leu Ala Gly Ala Tyr Ala Ile Ser Thr Leu Ile Lys Gln Lys Leu
                85                  90                  95
Asp Gly Leu Lys Asn Glu Gly Leu Lys Glu Lys Ile Asp Ala Ala Lys
                100                 105                 110
Lys Cys Ser Glu Thr Phe Thr Asn Lys Leu Lys Glu Lys His Thr Asp
                115                 120                 125
Leu Gly Lys Glu Gly Val Thr Asp Ala Asp Ala Lys Glu Ala Ile Leu
            130                 135                 140
Lys Ala Asn Gly Thr Lys Thr Lys Gly Ala Glu Glu Leu Gly Lys Leu
145                 150                 155                 160
Phe Glu Ser Val Glu Val Leu Ser Lys Ala Ala Lys Glu Met Leu Ala
                165                 170                 175
Asn Ser Val Lys Glu Leu Thr Ser Pro Val Val Ala Gly Ser Pro Lys
            180                 185                 190
Lys Pro Ser Met Ala Lys Gln Asn Val Ser Ser Leu Asp Glu Lys Asn
            195                 200                 205
Ser Val Ser Val Asp Leu Pro Gly Glu Met Lys Val Leu Val Ser Lys
210                 215                 220
Glu Lys Asn Lys Asp Gly Lys Tyr Asp Leu Ile Ala Thr Val Asp Lys
225                 230                 235                 240
Leu Glu Leu Lys Gly Thr Ser Asp Lys Asn Asn Gly Ser Gly Val Leu
                245                 250                 255
Glu Gly Val Lys Ala Asp Lys Ser Lys Val Lys Leu Thr Ile Ser Asp
            260                 265                 270
Asp Leu Gly Gln Thr Thr Leu Glu Val Phe Lys Glu Asp Gly Lys Thr
            275                 280                 285
Leu Val Ser Lys Lys Val Thr Ser Lys Asp Lys Ser Ser Thr Glu Glu
            290                 295                 300
Lys Phe Asn Glu Lys Gly Glu Val Ser Glu Lys Ile Ile Thr Arg Ala
305                 310                 315                 320
Asp Gly Thr Arg Leu Glu Tyr Thr Gly Ile Lys Ser Asp Gly Ser Gly
                325                 330                 335
Lys Ala Lys Glu Val Leu Lys Gly Tyr Val Leu Glu Gly Thr Leu Thr
                340                 345                 350
Ala Glu Lys Thr Thr Leu Val Val Lys Glu Gly Thr Val Thr Leu Ser
            355                 360                 365
Lys Asn Ile Ser Lys Ser Gly Glu Val Ser Val Glu Leu Asn Asp Thr
            370                 375                 380
Asp Ser Ser Ala Ala Thr Lys Lys Thr Ala Ala Trp Asn Ser Gly Thr
385                 390                 395                 400
Ser Thr Leu Thr Ile Thr Val Asn Ser Lys Lys Thr Lys Asp Leu Val
                405                 410                 415
Phe Thr Lys Glu Asn Thr Ile Thr Val Gln Gln Tyr Asp Ser Asn Gly
                420                 425                 430
Thr Lys Leu Glu Gly Ser Ala Val Glu Ile Thr Lys Leu Asp Glu Ile
            435                 440                 445
```

Lys Asn Ala Leu Lys
        450

<210> SEQ ID NO 11
<211> LENGTH: 440
<212> TYPE: PRT
<213> ORGANISM: Borrelia burgdorferi

<400> SEQUENCE: 11

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Val Ser Val Asp Leu Pro Gly Glu Met Lys Val
        195                 200                 205

Leu Val Ser Lys Glu Lys Asn Lys Asp Gly Lys Tyr Asp Leu Ile Ala
    210                 215                 220

Thr Val Asp Lys Leu Glu Leu Lys Gly Thr Ser Asp Lys Asn Asn Gly
225                 230                 235                 240

Ser Gly Val Leu Glu Gly Val Lys Ala Asp Lys Ser Lys Val Lys Leu
                245                 250                 255

Thr Ile Ser Asp Asp Leu Gly Gln Thr Thr Leu Glu Val Phe Lys Glu
            260                 265                 270

Asp Gly Lys Thr Leu Val Ser Lys Lys Val Thr Ser Lys Asp Lys Ser
        275                 280                 285

Ser Thr Glu Glu Lys Phe Asn Glu Lys Gly Glu Val Ser Glu Lys Ile
    290                 295                 300

Ile Thr Arg Ala Asp Gly Thr Arg Leu Glu Tyr Thr Gly Ile Lys Ser
305                 310                 315                 320

Asp Gly Ser Gly Lys Ala Lys Glu Val Leu Lys Gly Phe Thr Leu Glu
                325                 330                 335

Gly Lys Val Ala Asn Asp Lys Val Thr Leu Glu Val Lys Glu Gly Thr
            340                 345                 350

Val Thr Leu Ser Lys Ile Ser Lys Ser Gly Glu Val Ser Val Glu Leu
        355                 360                 365

Asn Asp Thr Asp Ser Ser Ala Ala Thr Lys Lys Thr Ala Ala Trp Asn
    370                 375                 380

Ser Lys Thr Ser Thr Leu Thr Ile Ser Val Asn Ser Lys Lys Thr Thr
385                 390                 395                 400

Gln Leu Val Phe Thr Lys Gln Asp Thr Ile Thr Val Gln Lys Tyr Asp
                405                 410                 415

Ser Ala Gly Thr Asn Leu Glu Gly Thr Ala Val Glu Ile Lys Thr Leu
                420                 425                 430

Asp Glu Leu Lys Asn Ala Leu Lys
            435                 440

<210> SEQ ID NO 12
<211> LENGTH: 405
<212> TYPE: PRT
<213> ORGANISM: Borrelia burgdorferi

<400> SEQUENCE: 12

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
                20                  25                  30

Ala Asp Glu Ser Val Lys Gly Pro Asn Leu Thr Glu Ile Asn Lys Lys
            35                  40                  45

Ile Thr Asp Ser Asn Ala Val Leu Leu Ala Val Lys Glu Val Glu Ala
    50                  55                  60

Leu Leu Ser Ser Ile Asp Glu Ile Ala Ala Lys Ala Ile Gly Lys Lys
65                  70                  75                  80

Ile His Gln Asn Asn Gly Leu Asp Thr Glu Asn Asn His Asn Gly Ser
                85                  90                  95

Leu Leu Ala Gly Ala Tyr Ala Ile Ser Thr Leu Ile Lys Gln Lys Leu
                100                 105                 110

Asp Gly Leu Lys Asn Glu Gly Leu Lys Glu Lys Ile Asp Ala Ala Lys
            115                 120                 125

Lys Cys Ser Glu Thr Phe Thr Asn Lys Leu Lys Glu Lys His Thr Asp
    130                 135                 140

Leu Gly Lys Glu Gly Val Thr Asp Ala Asp Ala Lys Glu Ala Ile Leu
145                 150                 155                 160

Lys Ala Asn Gly Thr Lys Thr Lys Gly Ala Glu Glu Leu Gly Lys Leu
                165                 170                 175

Phe Glu Ser Val Glu Val Leu Ser Lys Ala Ala Lys Glu Met Leu Ala
                180                 185                 190

Asn Ser Val Lys Glu Leu Thr Ser Pro Val Val Ala Glu Ser Pro Lys
            195                 200                 205

Lys Pro Ser Met Val Asn Asn Ser Gly Lys Asp Gly Asn Thr Ser Ala
    210                 215                 220

Asn Ser Ala Asp Glu Ser Val Lys Gly Pro Asn Leu Thr Glu Ile Ser
225                 230                 235                 240

Lys Lys Ile Thr Glu Ser Asn Ala Val Val Leu Ala Val Lys Glu Ile
                245                 250                 255

Glu Thr Leu Leu Ala Ser Ile Asp Glu Leu Ala Thr Lys Ala Ile Gly
                260                 265                 270

Lys Lys Ile Gln Gln Asn Gly Gly Leu Ala Val Glu Ala Gly His Asn
            275                 280                 285

Gly Thr Leu Leu Ala Gly Ala Tyr Thr Ile Ser Lys Leu Ile Thr Gln

```
                290                 295                 300
Lys Leu Asp Gly Leu Lys Asn Ser Glu Lys Leu Lys Glu Lys Ile Glu
305                 310                 315                 320

Asn Ala Lys Lys Cys Ser Glu Asp Phe Thr Lys Lys Leu Glu Gly Glu
                325                 330                 335

His Ala Gln Leu Gly Ile Glu Asn Val Thr Asp Glu Asn Ala Lys Lys
                340                 345                 350

Ala Ile Leu Ile Thr Asp Ala Ala Lys Asp Lys Gly Ala Ala Glu Leu
                355                 360                 365

Glu Lys Leu Phe Lys Ala Val Glu Asn Leu Ala Lys Ala Ala Lys Glu
                370                 375                 380

Met Leu Ala Asn Ser Val Lys Glu Leu Thr Ser Pro Ile Val Ala Glu
385                 390                 395                 400

Ser Pro Lys Lys Pro
                405

<210> SEQ ID NO 13
<211> LENGTH: 389
<212> TYPE: PRT
<213> ORGANISM: Borrelia burgdorferi

<400> SEQUENCE: 13

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Asn Lys Lys
                20                  25                  30

Ile Thr Asp Ser Asn Ala Val Leu Leu Ala Val Lys Val Glu Ala
                35                  40                  45

Leu Leu Ser Ser Ile Asp Glu Ile Ala Ala Lys Ala Ile Gly Lys Lys
50                  55                  60

Ile His Gln Asn Asn Gly Leu Asp Thr Glu Asn Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
                100                 105                 110

Lys Cys Ser Glu Thr Phe Thr Asn Lys Leu Lys Glu Lys His Thr Asp
                115                 120                 125

Leu Gly Lys Glu Gly Val Thr Asp Ala Asp Ala Lys Glu Ala Ile Leu
                130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Lys Glu Met Leu Ala
                165                 170                 175

Asn Ser Val Lys Glu Leu Thr Ser Pro Val Ala Glu Ser Pro Lys
                180                 185                 190

Lys Pro Ser Met Val Asn Asn Ser Gly Lys Asp Gly Asn Thr Ser Ala
                195                 200                 205

Asn Ser Ala Asp Glu Ser Val Lys Gly Pro Asn Leu Thr Glu Ile Ser
                210                 215                 220

Lys Lys Ile Thr Glu Ser Asn Ala Val Val Leu Ala Val Lys Glu Ile
225                 230                 235                 240

Glu Thr Leu Leu Ala Ser Ile Asp Glu Leu Ala Thr Lys Ala Ile Gly
                245                 250                 255
```

```
Lys Lys Ile Gln Gln Asn Gly Gly Leu Ala Val Glu Ala Gly His Asn
            260                 265                 270
Gly Thr Leu Leu Ala Gly Ala Tyr Thr Ile Ser Lys Leu Ile Thr Gln
            275                 280                 285
Lys Leu Asp Gly Leu Lys Asn Ser Glu Lys Leu Lys Glu Lys Ile Glu
            290                 295                 300
Asn Ala Lys Lys Cys Ser Glu Asp Phe Thr Lys Lys Leu Glu Gly Glu
305                 310                 315                 320
His Ala Gln Leu Gly Ile Glu Asn Val Thr Asp Glu Asn Ala Lys Lys
                325                 330                 335
Ala Ile Leu Ile Thr Asp Ala Ala Lys Asp Lys Gly Ala Ala Glu Leu
                340                 345                 350
Glu Lys Leu Phe Lys Ala Val Glu Asn Leu Ala Lys Ala Ala Lys Glu
            355                 360                 365
Met Leu Ala Asn Ser Val Lys Glu Leu Thr Ser Pro Ile Val Ala Glu
            370                 375                 380
Ser Pro Lys Lys Pro
385

<210> SEQ ID NO 14
<211> LENGTH: 470
<212> TYPE: PRT
<213> ORGANISM: Borrelia burgdorferi

<400> SEQUENCE: 14

Met Lys Lys Asn Thr Leu Ser Ala Ile Leu Met Thr Leu Phe Leu Phe
1               5                   10                  15
Ile Ser Cys Asn Asn Ser Gly Lys Asp Gly Asn Thr Ser Ala Asn Ser
            20                  25                  30
Ala Asp Glu Ser Val Lys Gly Pro Asn Leu Thr Glu Ile Ser Lys Lys
            35                  40                  45
Ile Thr Glu Ser Asn Ala Val Val Leu Ala Val Lys Glu Ile Glu Thr
        50                  55                  60
Leu Leu Ala Ser Ile Asp Glu Leu Ala Thr Lys Ala Ile Gly Lys Lys
65                  70                  75                  80
Ile Gln Gln Asn Gly Gly Leu Ala Val Glu Ala Gly His Asn Gly Thr
                85                  90                  95
Leu Leu Ala Gly Ala Tyr Thr Ile Ser Lys Leu Ile Thr Gln Lys Leu
            100                 105                 110
Asp Gly Leu Lys Asn Ser Glu Lys Leu Lys Glu Lys Ile Glu Asn Ala
            115                 120                 125
Lys Lys Cys Ser Glu Asp Phe Thr Lys Lys Leu Glu Gly Glu His Ala
        130                 135                 140
Gln Leu Gly Ile Glu Asn Val Thr Asp Glu Asn Ala Lys Lys Ala Ile
145                 150                 155                 160
Leu Ile Thr Asp Ala Ala Lys Asp Lys Gly Ala Ala Glu Leu Glu Lys
                165                 170                 175
Leu Phe Lys Ala Val Glu Asn Leu Ala Lys Ala Ala Lys Glu Met Leu
            180                 185                 190
Ala Asn Ser Val Lys Glu Leu Thr Ser Pro Ile Val Ala Glu Ser Pro
            195                 200                 205
Lys Lys Pro Ser Met Ala Lys Gln Asn Val Ser Ser Leu Asp Glu Lys
        210                 215                 220
Asn Ser Val Ser Val Asp Leu Pro Gly Glu Met Lys Val Leu Val Ser
225                 230                 235                 240
```

Lys Glu Lys Asn Lys Asp Gly Lys Tyr Asp Leu Ile Ala Thr Val Asp
              245                 250                 255

Lys Leu Glu Leu Lys Gly Thr Ser Asp Lys Asn Asn Gly Ser Gly Val
              260                 265                 270

Leu Glu Gly Val Lys Ala Asp Lys Ser Lys Val Lys Leu Thr Ile Ser
              275                 280                 285

Asp Asp Leu Gly Gln Thr Thr Leu Glu Val Phe Lys Glu Asp Gly Lys
              290                 295                 300

Thr Leu Val Ser Lys Lys Val Thr Ser Lys Asp Lys Ser Ser Thr Glu
305                 310                 315                 320

Glu Lys Phe Asn Glu Lys Gly Glu Val Ser Lys Ile Ile Thr Arg
              325                 330                 335

Ala Asp Gly Thr Arg Leu Glu Tyr Thr Gly Ile Lys Ser Asp Gly Ser
              340                 345                 350

Gly Lys Ala Lys Glu Val Leu Lys Gly Tyr Val Leu Glu Gly Thr Leu
              355                 360                 365

Thr Ala Glu Lys Thr Thr Leu Val Val Lys Glu Gly Thr Val Thr Leu
              370                 375                 380

Ser Lys Asn Ile Ser Lys Ser Gly Glu Val Ser Val Glu Leu Asn Asp
385                 390                 395                 400

Thr Asp Ser Ser Ala Ala Thr Lys Lys Thr Ala Ala Trp Asn Ser Gly
              405                 410                 415

Thr Ser Thr Leu Thr Ile Thr Val Asn Ser Lys Lys Thr Lys Asp Leu
              420                 425                 430

Val Phe Thr Lys Glu Asn Thr Ile Thr Val Gln Gln Tyr Asp Ser Asn
              435                 440                 445

Gly Thr Lys Leu Glu Gly Ser Ala Val Glu Ile Thr Lys Leu Asp Glu
              450                 455                 460

Ile Lys Asn Ala Leu Lys
465                 470

<210> SEQ ID NO 15
<211> LENGTH: 470
<212> TYPE: PRT
<213> ORGANISM: Borrelia burgdorferi

<400> SEQUENCE: 15

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
              20                  25                  30

Ala Asp Glu Ser Val Lys Gly Pro Asn Leu Thr Glu Ile Ser Lys Lys
              35                  40                  45

Ile Thr Glu Ser Asn Ala Val Val Leu Ala Val Lys Glu Ile Glu Thr
50                  55                  60

Leu Leu Ala Ser Ile Asp Glu Leu Ala Thr Lys Ala Ile Gly Lys Lys
65                  70                  75                  80

Ile Gln Gln Asn Gly Gly Leu Ala Val Glu Ala Gly His Asn Gly Thr
              85                  90                  95

Leu Leu Ala Gly Ala Tyr Thr Ile Ser Lys Leu Ile Thr Gln Lys Leu
              100                 105                 110

Asp Gly Leu Lys Asn Ser Glu Lys Leu Lys Glu Lys Ile Glu Asn Ala
              115                 120                 125

Lys Lys Cys Ser Glu Asp Phe Thr Lys Lys Leu Glu Gly Glu His Ala

```
            130                 135                 140
Gln Leu Gly Ile Glu Asn Val Thr Asp Glu Asn Ala Lys Lys Ala Ile
145                 150                 155                 160

Leu Ile Thr Asp Ala Ala Lys Asp Lys Gly Ala Ala Glu Leu Glu Lys
                165                 170                 175

Leu Phe Lys Ala Val Glu Asn Leu Ala Lys Ala Lys Glu Met Leu
                180                 185                 190

Ala Asn Ser Val Lys Glu Leu Thr Ser Pro Ile Val Ala Glu Ser Pro
                195                 200                 205

Lys Lys Pro Ser Met Ala Lys Gln Asn Val Ser Ser Leu Asp Glu Lys
                210                 215                 220

Asn Ser Val Ser Val Asp Leu Pro Gly Glu Met Lys Val Leu Val Ser
225                 230                 235                 240

Lys Glu Lys Asn Lys Asp Gly Lys Tyr Asp Leu Ile Ala Thr Val Asp
                245                 250                 255

Lys Leu Glu Leu Lys Gly Thr Ser Asp Lys Asn Asn Gly Ser Gly Val
                260                 265                 270

Leu Glu Gly Val Lys Ala Asp Lys Ser Lys Val Lys Leu Thr Ile Ser
                275                 280                 285

Asp Asp Leu Gly Gln Thr Thr Leu Glu Val Phe Lys Glu Asp Gly Lys
290                 295                 300

Thr Leu Val Ser Lys Lys Val Thr Ser Lys Asp Lys Ser Ser Thr Glu
305                 310                 315                 320

Glu Lys Phe Asn Glu Lys Gly Glu Val Ser Glu Lys Ile Ile Thr Arg
                325                 330                 335

Ala Asp Gly Thr Arg Leu Glu Tyr Thr Gly Ile Lys Ser Asp Gly Ser
                340                 345                 350

Gly Lys Ala Lys Glu Val Leu Lys Gly Phe Thr Leu Glu Gly Lys Val
                355                 360                 365

Ala Asn Asp Lys Val Thr Leu Glu Val Lys Glu Gly Thr Val Thr Leu
                370                 375                 380

Ser Lys Asn Ile Ser Lys Ser Gly Glu Val Ser Val Glu Leu Asn Asp
385                 390                 395                 400

Thr Asp Ser Ser Ala Ala Thr Lys Lys Thr Ala Ala Trp Asn Ser Lys
                405                 410                 415

Thr Ser Thr Leu Thr Ile Ser Val Asn Ser Lys Lys Thr Thr Gln Leu
                420                 425                 430

Val Phe Thr Lys Gln Asp Thr Ile Thr Val Gln Lys Tyr Asp Ser Ala
                435                 440                 445

Gly Thr Asn Leu Glu Gly Thr Ala Val Glu Ile Lys Thr Leu Asp Glu
                450                 455                 460

Leu Lys Asn Ala Leu Lys
465                 470

<210> SEQ ID NO 16
<211> LENGTH: 454
<212> TYPE: PRT
<213> ORGANISM: Borrelia burgdorferi

<400> SEQUENCE: 16

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
                20                  25                  30
```

-continued

```
Ile Thr Glu Ser Asn Ala Val Val Leu Ala Val Lys Glu Ile Glu Thr
             35                  40                  45

Leu Leu Ala Ser Ile Asp Glu Leu Ala Thr Lys Ala Ile Gly Lys Lys
 50                  55                  60

Ile Gln Gln Asn Gly Gly Leu Ala Val Glu Ala Gly His Asn Gly Thr
 65                  70                  75                  80

Leu Leu Ala Gly Ala Tyr Thr Ile Ser Lys Leu Ile Thr Gln Lys Leu
                 85                  90                  95

Asp Gly Leu Lys Asn Ser Glu Lys Leu Lys Glu Lys Ile Glu Asn Ala
                100                 105                 110

Lys Lys Cys Ser Glu Asp Phe Thr Lys Lys Leu Glu Gly Glu His Ala
            115                 120                 125

Gln Leu Gly Ile Glu Asn Val Thr Asp Glu Asn Ala Lys Lys Ala Ile
        130                 135                 140

Leu Ile Thr Asp Ala Ala Lys Asp Lys Gly Ala Ala Glu Leu Glu Lys
145                 150                 155                 160

Leu Phe Lys Ala Val Glu Asn Leu Ala Lys Ala Lys Glu Met Leu
                165                 170                 175

Ala Asn Ser Val Lys Glu Leu Thr Ser Pro Ile Val Ala Glu Ser Pro
            180                 185                 190

Lys Lys Pro Ser Met Ala Lys Gln Asn Val Ser Ser Leu Asp Glu Lys
        195                 200                 205

Asn Ser Val Ser Val Asp Leu Pro Gly Glu Met Lys Val Leu Val Ser
    210                 215                 220

Lys Glu Lys Asn Lys Asp Gly Lys Tyr Asp Leu Ile Ala Thr Val Asp
225                 230                 235                 240

Lys Leu Glu Leu Lys Gly Thr Ser Asp Lys Asn Asn Gly Ser Gly Val
                245                 250                 255

Leu Glu Gly Val Lys Ala Asp Lys Ser Lys Val Lys Leu Thr Ile Ser
            260                 265                 270

Asp Asp Leu Gly Gln Thr Thr Leu Glu Val Phe Lys Glu Asp Gly Lys
        275                 280                 285

Thr Leu Val Ser Lys Lys Val Thr Ser Lys Asp Lys Ser Ser Thr Glu
290                 295                 300

Glu Lys Phe Asn Glu Lys Gly Glu Val Ser Glu Lys Ile Ile Thr Arg
305                 310                 315                 320

Ala Asp Gly Thr Arg Leu Glu Tyr Thr Gly Ile Lys Ser Asp Gly Ser
                325                 330                 335

Gly Lys Ala Lys Glu Val Leu Lys Gly Tyr Val Leu Glu Gly Thr Leu
            340                 345                 350

Thr Ala Glu Lys Thr Thr Leu Val Val Lys Glu Gly Thr Val Thr Leu
        355                 360                 365

Ser Lys Asn Ile Ser Lys Ser Gly Glu Val Ser Val Glu Leu Asn Asp
    370                 375                 380

Thr Asp Ser Ser Ala Ala Thr Lys Lys Thr Ala Ala Trp Asn Ser Gly
385                 390                 395                 400

Thr Ser Thr Leu Thr Ile Thr Val Asn Ser Lys Lys Thr Lys Asp Leu
                405                 410                 415

Val Phe Thr Lys Glu Asn Thr Ile Thr Val Gln Gln Tyr Asp Ser Asn
            420                 425                 430

Gly Thr Lys Leu Glu Gly Ser Ala Val Glu Ile Thr Lys Leu Asp Glu
        435                 440                 445

Ile Lys Asn Ala Leu Lys
```

<210> SEQ ID NO 17
<211> LENGTH: 454
<212> TYPE: PRT
<213> ORGANISM: Borrelia burgdorferi

<400> SEQUENCE: 17

```
Met Ala Cys Asn Asn Ser Gly Lys Asp Gly Asn Thr Ser Ala Asn Ser
1               5                   10                  15
Ala Asp Glu Ser Val Lys Gly Pro Asn Leu Thr Glu Ile Ser Lys Lys
            20                  25                  30
Ile Thr Glu Ser Asn Ala Val Val Leu Ala Val Lys Glu Ile Glu Thr
        35                  40                  45
Leu Leu Ala Ser Ile Asp Glu Leu Ala Thr Lys Ala Ile Gly Lys Lys
    50                  55                  60
Ile Gln Gln Asn Gly Gly Leu Ala Val Glu Ala Gly His Asn Gly Thr
65                  70                  75                  80
Leu Leu Ala Gly Ala Tyr Thr Ile Ser Lys Leu Ile Thr Gln Lys Leu
                85                  90                  95
Asp Gly Leu Lys Asn Ser Glu Lys Leu Lys Glu Lys Ile Glu Asn Ala
            100                 105                 110
Lys Lys Cys Ser Glu Asp Phe Thr Lys Lys Leu Glu Gly Glu His Ala
        115                 120                 125
Gln Leu Gly Ile Glu Asn Val Thr Asp Glu Asn Ala Lys Lys Ala Ile
    130                 135                 140
Leu Ile Thr Asp Ala Ala Lys Asp Lys Gly Ala Ala Glu Leu Glu Lys
145                 150                 155                 160
Leu Phe Lys Ala Val Glu Asn Leu Ala Lys Ala Ala Lys Glu Met Leu
                165                 170                 175
Ala Asn Ser Val Lys Glu Leu Thr Ser Pro Ile Val Ala Glu Ser Pro
            180                 185                 190
Lys Lys Pro Ser Met Ala Lys Gln Asn Val Ser Ser Leu Asp Glu Lys
        195                 200                 205
Asn Ser Val Ser Val Asp Leu Pro Gly Glu Met Lys Val Leu Val Ser
    210                 215                 220
Lys Glu Lys Asn Lys Asp Gly Lys Tyr Asp Leu Ile Ala Thr Val Asp
225                 230                 235                 240
Lys Leu Glu Leu Lys Gly Thr Ser Asp Lys Asn Asn Gly Ser Gly Val
                245                 250                 255
Leu Glu Gly Val Lys Ala Asp Lys Ser Lys Val Lys Leu Thr Ile Ser
            260                 265                 270
Asp Asp Leu Gly Gln Thr Thr Leu Glu Val Phe Lys Glu Asp Gly Lys
        275                 280                 285
Thr Leu Val Ser Lys Lys Val Thr Ser Lys Asp Lys Ser Ser Thr Glu
    290                 295                 300
Glu Lys Phe Asn Glu Lys Gly Glu Val Ser Glu Lys Ile Ile Thr Arg
305                 310                 315                 320
Ala Asp Gly Thr Arg Leu Glu Tyr Thr Gly Ile Lys Ser Asp Gly Ser
                325                 330                 335
Gly Lys Ala Lys Glu Val Leu Lys Gly Phe Thr Leu Glu Gly Lys Val
            340                 345                 350
Ala Asn Asp Lys Val Thr Leu Glu Val Lys Glu Gly Thr Val Thr Leu
        355                 360                 365
```

```
Ser Lys Asn Ile Ser Lys Ser Gly Glu Val Ser Val Glu Leu Asn Asp
    370                 375                 380
Thr Asp Ser Ser Ala Ala Thr Lys Lys Thr Ala Ala Trp Asn Ser Lys
385                 390                 395                 400
Thr Ser Thr Leu Thr Ile Ser Val Asn Ser Lys Lys Thr Thr Gln Leu
                405                 410                 415
Val Phe Thr Lys Gln Asp Thr Ile Thr Val Gln Lys Tyr Asp Ser Ala
            420                 425                 430
Gly Thr Asn Leu Glu Gly Thr Ala Val Glu Ile Lys Thr Leu Asp Glu
        435                 440                 445
Leu Lys Asn Ala Leu Lys
    450

<210> SEQ ID NO 18
<211> LENGTH: 326
<212> TYPE: PRT
<213> ORGANISM: Yersinia pestis

<400> SEQUENCE: 18

Met Ile Arg Ala Tyr Glu Gln Asn Pro Gln His Phe Ile Glu Asp Leu
1               5                   10                  15
Glu Lys Val Arg Val Glu Gln Leu Thr Gly His Gly Ser Ser Val Leu
            20                  25                  30
Glu Glu Leu Val Gln Leu Val Lys Asp Lys Asn Ile Asp Ile Ser Ile
        35                  40                  45
Lys Tyr Asp Pro Arg Lys Asp Ser Glu Val Phe Ala Asn Arg Val Ile
    50                  55                  60
Thr Asp Asp Ile Glu Leu Leu Lys Lys Ile Leu Ala Tyr Phe Leu Pro
65                  70                  75                  80
Glu Asp Ala Ile Leu Lys Gly Gly His Tyr Asp Asn Gln Leu Gln Asn
                85                  90                  95
Gly Ile Lys Arg Val Lys Glu Phe Leu Glu Ser Ser Pro Asn Thr Gln
            100                 105                 110
Trp Glu Leu Arg Ala Phe Met Ala Val Met His Phe Ser Leu Thr Ala
        115                 120                 125
Asp Arg Ile Asp Asp Ile Leu Lys Val Ile Val Asp Ser Met Asn
    130                 135                 140
His His Gly Asp Ala Arg Ser Lys Leu Arg Glu Glu Leu Ala Glu Leu
145                 150                 155                 160
Thr Ala Glu Leu Lys Ile Tyr Ser Val Ile Gln Ala Glu Ile Asn Lys
                165                 170                 175
His Leu Ser Ser Ser Gly Thr Ile Asn Ile His Asp Lys Ser Ile Asn
            180                 185                 190
Leu Met Asp Lys Asn Leu Tyr Gly Tyr Thr Asp Glu Gly Ile Phe Lys
        195                 200                 205
Ala Ser Ala Glu Tyr Lys Ile Leu Glu Lys Met Pro Gln Thr Thr Ile
    210                 215                 220
Gln Val Asp Gly Ser Glu Lys Lys Ile Val Ser Ile Lys Asp Phe Leu
225                 230                 235                 240
Gly Ser Glu Asn Lys Arg Thr Gly Ala Leu Gly Asn Leu Lys Asn Ser
                245                 250                 255
Tyr Ser Tyr Asn Lys Asp Asn Asn Glu Leu Ser His Phe Ala Thr Thr
            260                 265                 270
Cys Ser Asp Lys Ser Arg Pro Leu Asn Asp Leu Val Ser Gln Lys Thr
        275                 280                 285
```

```
Thr Gln Leu Ser Asp Ile Thr Ser Arg Phe Asn Ser Ala Ile Glu Ala
        290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 19
<211> LENGTH: 170
<212> TYPE: PRT
<213> ORGANISM: Yersinia pestis

<400> SEQUENCE: 19

Met Lys Lys Ile Ser Ser Val Ile Ala Ile Ala Leu Phe Gly Thr Ile
1               5                   10                  15

Ala Thr Ala Asn Ala Ala Asp Leu Thr Ala Ser Thr Thr Ala Thr Ala
                20                  25                  30

Thr Leu Val Glu Pro Ala Arg Ile Thr Leu Thr Tyr Lys Glu Gly Ala
            35                  40                  45

Pro Ile Thr Ile Met Asp Asn Gly Asn Ile Asp Thr Glu Leu Leu Val
        50                  55                  60

Gly Thr Leu Thr Leu Gly Gly Tyr Lys Thr Gly Thr Thr Ser Thr Ser
65                  70                  75                  80

Val Asn Phe Thr Asp Ala Ala Gly Asp Pro Met Tyr Leu Thr Phe Thr
                85                  90                  95

Ser Gln Asp Gly Asn Asn His Gln Phe Thr Thr Lys Val Ile Gly Lys
            100                 105                 110

Asp Ser Arg Asp Phe Asp Ile Ser Pro Lys Val Asn Gly Glu Asn Leu
        115                 120                 125

Val Gly Asp Asp Val Val Leu Ala Thr Gly Ser Gln Asp Phe Phe Val
    130                 135                 140

Arg Ser Ile Gly Ser Lys Gly Gly Lys Leu Ala Ala Gly Lys Tyr Thr
145                 150                 155                 160

Asp Ala Val Thr Val Thr Val Ser Asn Gln
                165                 170
```